United States Patent [19]

Bossert et al.

[11] 4,044,141

[45] Aug. 23, 1977

[54] 1,4-DIHYDROPYRIDINES

[75] Inventors: Friedrich Bossert, Wuppertal; Egbert Wehinger, Neviges; Kurt Stoepel, Wuppertal; Wulf Vater, Leverkusen; Stanislav Kazda, Wuppertal, all of Germany

[73] Assignee: Bayer Aktiengesellschaft, Germany

[21] Appl. No.: 654,278

[22] Filed: Feb. 2, 1976

[30] Foreign Application Priority Data

Feb. 26, 1975 Germany .............................. 2508181

[51] Int. Cl.$^2$ .................. A61K 31/455; C07D 213/55
[52] U.S. Cl. ............................. 424/266; 260/256.4 R; 260/287 R; 260/287 D; 260/294.8 D; 260/294.8 F; 260/294.8 G; 260/294.9; 260/295.5 R; 260/295.5 B
[58] Field of Search ..................... 260/295.5 R, 294.9, 260/294.8 G, 294.8 F; 424/266

[56] References Cited

U.S. PATENT DOCUMENTS 3,996,234   12/1976   Bossert et al. ................ 260/295.5 R

*Primary Examiner*—Alan L. Rotman
*Attorney, Agent, or Firm*—Jacobs & Jacobs

[57] ABSTRACT

1,4-Dihydropyridines characterized by a carbo(arylalkoxy) group in the 5-position, an aryl group in the 4-position and a alkanoyl or carbalkoxy group in the 3-position and further optionally substituted in the 1,2 and 6-positions are coronary dilating, spasmolytic and hypotensive agents. The compounds, of which 2,6-dimethyl-3-carbomethoxy-4-(2-nitrophenyl)-5-carbobenzoxy-1,4-dihydropyridine is a representative embodiment, are prepared through the reaction of an ylidene-β-dicarbonyl compound, which may be generated in situ from the corresponding β-dicarbonyl compound and an aldehyde, and an enaminocarboxylic acid ester, which may also be generated in situ from a β-dicarbonyl compound and an amine.

22 Claims, No Drawings

1,4-DIHYDROPYRIDINES

DETAILED DESCRIPTION

The present invention relates to new 1,4-dihydropyridinecarboxylic acid aralkyl esters, to processes for their preparation, and to their use as coronary, spasmolytic and antihypertensive agents.

It is known that 2,6-dimethyl-4-phenyl-1,4-dihydropyridine-3,5-dicarboxylic acid diesters are obtained when benzylideneacetoacetic acid ethyl ester is reacted with β-aminocrotonic acid ethyl ester or acetoacetic acid ethyl ester and ammonia; see e.g., Knoevenagel, Ber. dtsch. chem. Ges. 31, 743 (1898). It is also known that certain 1,4-dihydropyridines exhibit interesting pharmacological properties; see e.g., F. Bossert and W. Vater, Die Naturwissenschaften 58, 578 (1971).

The present invention pertains to a new class of 1,4-dihydropyridines which exhibit especially potent coronary and antihypertensive effects, in particular a greater antihypertensive effective on the blood vessels than any known dihydropyridine.

In particular, the present invention pertains to compounds of the formula:

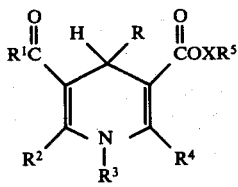

I wherein
- R is a phenyl or naphthyl group unsubstituted or substituted with from one to three sterically permissible substituents selected from the group consisting of phenyl, lower alkyl, alkenyl, alkinyl, alkoxy, halo, trifluoromethoxy, trifluoromethyl, nitro, azido, cyano, hydroxy, amino, carbo(lower alkoxy), carbamido, sulfonamido, (lower alkoxy)thio, (lower alkyl)sulfinyl or (lower alkyl)sulfonyl, or a quinolyl, isoquinolyl, pyridyl, pyrimidyl, thienyl, furyl or pyrryl group unsubstituted or substituted by lower alkyl, lower alkoxy or halo;
- $R^1$ represents alkyl or the —$OR^6$ group, wherein $R^6$ represents a straight chain, branched or cyclic, saturated or unsaturated hydrocarbon radical which is optionally interrupted by 1 or 2 oxygen atoms in the chain or in which a hydrogen atom is substituted by an hydroxyl or amino group, and the latter optionally carries two identical or different substituents from the group of alkyl, alkoxyalkyl, aryl and aralkyl, and these substituents optionally form a 5-membered to 7-membered ring with the amine nitrogen,
- $R^2$ and $R^4$ are identical or different and represent hydrogen or a straight-chain or branched alkyl radical,
- $R^3$ is hydrogen, lower alkyl or (lower alkoxy)lower alkyl;
- $R^5$ is a phenyl, phenoxy or phenylthio group unsubstituted or substituted with from one to three sterically permissible substituents selected from the group consisting of lower alkyl, lower alkoxy, halo, trifluoromethyl, trifluoromethoxy, hydroxy, amino, di(lower alkyl)amino, nitro, cyano, carbamido, sulfonamido, (lower alkyl)thio, (lower alkyl)sulfinyl, a (lower alkyl)sulfonyl and
- X is lower alkylene.

In one embodiment, the invention pertains to compounds of Formula I wherein
- R is pyridyl, phenyl or phenyl unsubstituted or substituted with lower alkyl, lower alkoxy, halo, trifluoromethyl, nitro, azido or cyano;
- $R^1$ is lower alkyl, lower alkoxy, cycloalkoxy or (lower alkoxy)lower alkoxy;
- each of $R^2$ and $R^4$ is methyl;
- $R^3$ is hydrogen or methyl;
- $R^5$ is a phenyl or phenoxy group unsubstituted or substituted with one to three sterically permissible substituents selected from the group consisting of lower alkyl, lower alkoxy, halo, trifluoromethyl and nitro; and
- X is lower alkylene.

In a further embodiment, the invention pertains to compounds of Formula I wherein
- R is pyridyl, phenyl, nitrophenyl, trifluoromethylphenyl, chlorophenyl or cyanophenyl;
- $R^1$ is methyl, methoxy, ethoxy, isopropoxy, isobutoxy, cyclopentoxy, cyclohexoxy or methoxyethoxy;
- each of $R^2$ and $R^4$ is methyl;
- $R^3$ is hydrogen or methyl;
- $R^5$ is phenoxy, phenyl, chlorophenyl, dichlorophenyl, methylphenyl, t.-butylphenyl, methoxyphenyl, dimethoxyphenyl, trimethoxyphenyl, trifluoromethylphenyl or nitrophenyl; and
- X is methylene, ethylene, ethylidene, trimethylene or 1,2-propylene.

In a further embodiment, the invention pertains to compounds of Formula I wherein
- R is phenyl or nitrophenyl;
- $R^1$ is methoxy or isopropoxy;
- each of $R^2$ and $R^4$ is methyl;
- $R^3$ is hydrogen;
- $R^5$ is phenyl, chlorophenyl or trifluoromethylphenyl; and
- X is methylene.

In a further embodiment, the invention pertains to compounds of Formula I wherein
- R is 2-nitrophenyl or 3-nitrophenyl;
- $R^1$ is methoxy or isopropoxy;
- each of $R^2$ and $R^4$ is methyl;
- $R^3$ is hydrogen;
- $R^5$ is phenyl, 3-chlorophenyl, 4-chlorophenyl, 3-trifluoromethylphenyl or 4-trifluoromethylphenyl; and
- X is methylene.

The term alkyl denotes a univalent saturated branched or straight hydrocarbon chain containing from 1 to 18 carbon atoms. Representative of such alkyl groups are thus methyl, ethyl, propyl, isopropyl, butyl, isobutyl, sec-butyl, tert-butyl, pentyl, isopentyl, neopentyl, tert-pentyl, hexyl, isohexyl, heptyl, octyl, nonyl, decyl, undecyl, dodecyl, tridecyl, tetradecyl, pentadecyl, hexadecyl, heptadecyl, octadecyl, and the like.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec-butyl, tert-butyl, pentyl, isopentyl, neopentyl, tert-pentyl, hexyl, and the like.

The term cycloalkyl denotes a univalent saturated monocyclic hydrocarbon of from 3 to 7 carbon atoms as, for example, cyclopropyl, cyclobutyl, cyclopentyl, cyclohexyl, and cycloheptyl.

The term lower alkoxy denotes a straight or branched hydrocarbon chain of 1 to 6 carbon atoms bound to the remainder of the molecule through a divalent oxygen atom as, for example, methoxy, ethoxy, propoxy, isopropoxy, butoxy, isobutoxy, pentoxy and hexoxy.

The term lower alkylthio denotes a branched or straight hydrocarbon chain of 1 to 6 carbon atoms bound to the remainder of the molecule through a divalent sulfur as, for example, methylthio, ethylthio, propylthio, isopropylthio, butylthio, and the like.

The term halo denotes the monovalent substituents fluoro, chloro, bromo and iodo.

The compounds of the present invention can exist as optical isomers and both the racemates of these isomers and the individual isomers themselves are within the scope of the present invention. The racemates can be separated into their individual isomers through the well known technique such as forming and separating diastereomeric compounds.

The compounds of the present invention are prepared by a process which comprises allowing (a) an ylidene of the formula

$$\underset{R^7COCCOR^9}{\overset{\overset{\displaystyle RCH}{\|}}{}}$$

or (b) the elements thereof consisting of a β-dicarbonyl compound of the formula $$R^7COCH_2COR^9$$

and an aldehyde of the formula RCHO to react with (c) an enaminocarboxylic acid ester of the formula

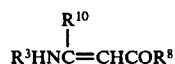
$$\underset{R^3HNC=CHCOR^8}{\overset{R^{10}}{|}}$$

or (d) the elements thereof consisting of a ketocarboxylic acid ester of the formula $$R^{10}COCH_2COR^8$$

and an amine of the formula $R^3NH_2$ wherein either (i) $R^7$ corresponds to $R^1$, $R^8$ corresponds to -$OXR^5$, $R^9$ corresponds to $R^2$ and $R^{10}$ corresponds to $R^4$ or (ii) $R^7$ corresponds to -$OXR^5$, $R^8$ corresponds to $R^1$, $R^9$ corresponds to $R^4$ and $R^{10}$ corresponds to $R^2$, and each of R, $R^1$, $R^2$, $R^3$, $R^4$, $R^5$ and X are as herein defined.

It will be observed that this process has a number of variables as to reactants. In one of these process variants, a ylidene is allowed to react with an enaminocarboxylic acid ester. The ylidene-β-dicarbonyl compound can correspond to compounds of the formula

$$\underset{R^1COCCOR^2}{\overset{\overset{\displaystyle RCH}{\|}}{}} \qquad \text{II}$$

in which case the enaminocarboxylic acid ester corresponds to compounds of the formula $$\underset{R^3HNC=CHCOOXR^5}{\overset{R^4}{|}} \qquad \text{III}$$

In lieu of the enaminocarboxylic acid ester, one can employ the elements thereof, namely an amine of the formula $$R^3NH_2 \qquad \text{IV}$$

and a β-ketocarboxylic acid ester of the formula $$R^4COCH_2COOXR^5 \qquad \text{V.}$$

Alternatively, the ylidene-β-dicarbonyl compound can correspond to compounds of the formula

$$\underset{R^5XOCOCCOR^4}{\overset{\overset{\displaystyle RCH}{\|}}{}} \qquad \text{VI}$$

in which case the enaminocarboxylic acid ester will correspond to compounds of the formula $$\underset{R^3HNC=CHCOR^1}{\overset{R^2}{|}} \qquad \text{VII}$$

Here again, the elements of the enaminocarboxylic acid can be used in lieu thereof, namely an amine of Formula IV and a β-dicarbonyl compound of the formula $$R^2COCH_2COR^1 \qquad \text{VIII.}$$

Alternately the foregoing ylidene compounds can be replaced by the elements thereof. Thus an enaminocarboxylic acid ester of Formula III can be reacted with an aldehyde of the formula $$RCHO \qquad \text{IX}$$

with the β-dicarbonyl compound of Formula VIII or an enaminocarboxylic acid of Formula VII can be reacted with the aldehyde of Formula IX and the β-ketocarboxylic acid ester of Formula V.

Utilizing 2,6-dimethyl-3-carbisopropoxy-4-(3-nitrophenyl)-1,4-dihydropyridine-5-carboxylic acid benzyl ester (IA) as a representative example, the first two of these process variants can be represented as follows:

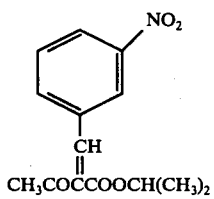

(IIA)

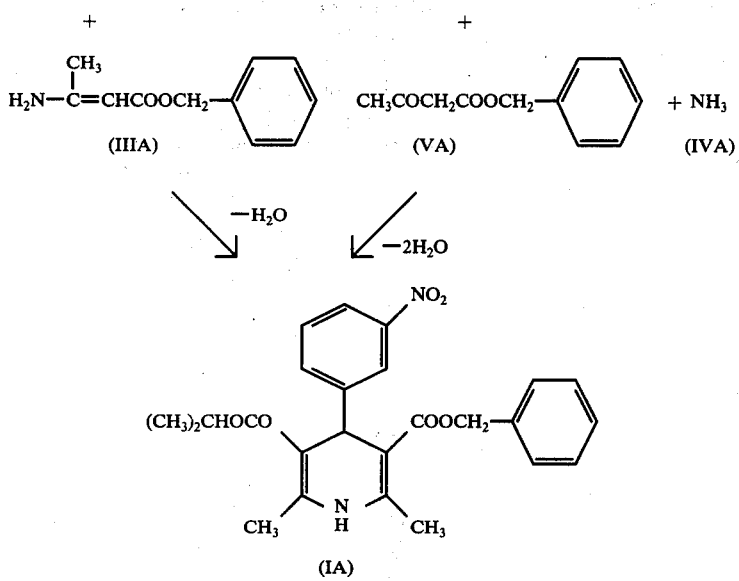

Utilizing 2,6-dimethyl-3-carbethoxy-4-(2-chlorophenyl)-1,4-dihydropyridine-5-carboxylic acid 4-chlorobenzyl ester (IB) as a representative example, the third and fourth of these process variants can be represented as follows:

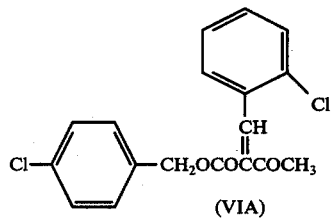

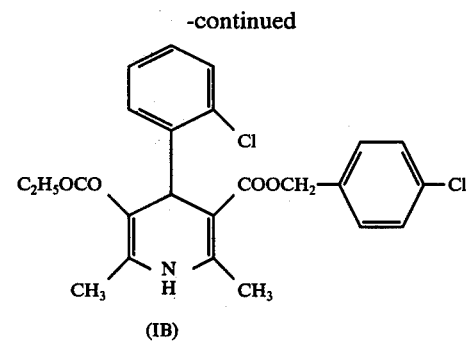

Utilizing the same example, the fifth and sixth of these process variants can be represented as follows:

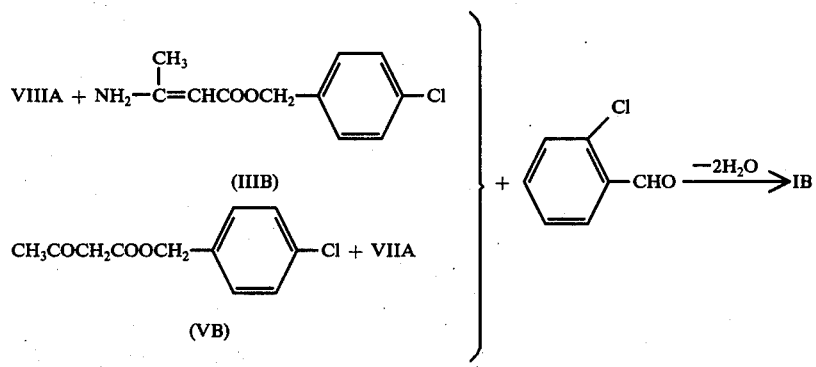

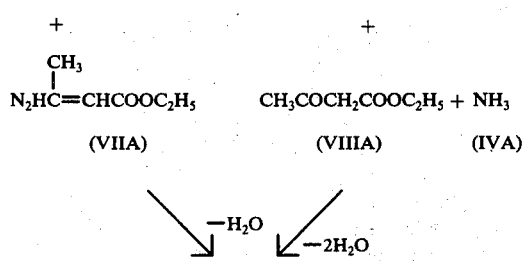

The ylidene-β-dicarbonyl compounds of Formula II are known or can be prepared according to known methods; see e.g., Org. Reactions XV, 204 et seq. (1967). Typical examples include benzylideneacetoacetic acid methyl ester, 2'-nitrobenzylideneacetoacetic acid methyl ester, 2'-nitrobenzylideneacetylacetone, benzylideneacetylacetone, 3'-nitrobenzylideneacetoacetic acid methyl ester, 3'-nitrobenzylideneacetoacetic acid propargyl ester, 3'-nitrobenzylideneacetoacetic acid allyl ester, 3'-nitrobenzylideneacetoacetic acid β-methoxyethyl ester, 3'-nitrobenzylideneacetoacetic acid β-ethoxyethyl ester, 3'-nitrobenzylideneacetoacetic acid isopropyl ester, 3'-nitrobenzylideneacetylacetone, 4'-nitrobenzylideneacetylacetone, 4'-nitrobenzylideneacetoacetic acid β-propoxyethyl ester, 4'-nitrobenzylideneacetoacetic acid n-propyl ester, 3'-nitro-6'-chlorobenzylideneacetoacetic acid methyl ester, 2'-cyano-benzylideneacetoacetic acid methyl ester, 2'-cyanobenzylideneacetoacetic acid ethyl ester, 2'-cyanobenzylidenepriopionylacetic acid ethyl ester, 3'-cyanobenzylideneacetoacetic acid methyl ester, 2'-, 3'- or 4'-methoxybenzylideneacetoacetic acid ethyl ester, 2'-, 3'- or 4'-methoxybenzylideneacetylacetone, 2'-methoxybenzylideneacetoacetic acid allyl ester, 2'-methoxybenzylideneacetoacetic acid β-methoxyethyl ester, 2'-isopropoxybenzylideneacetoacetic acid ethyl ester, 3'-butoxybenzylideneacetoacetic acid methyl ester, 3',4',5'-trimethoxybenzylideneacetoacetic acid allyl ester, 2'-methylbenzylidenepropionylacetic acid methyl ester, 2'-, 3'- or 4'-methylbenzylideneacetoacetic acid ethyl ester, 2'-methylbenzylideneacetoacetic acid β-methoxyethyl ester, 2'-methylbenzylideneacetoacetic acid β-propoxyethyl ester, 2'-methylbenzylideneacetylacetone, 2'-cyclopropyl-benzylideneacetoacetic acid ethyl ester, 2'-ethinyl-benzylideneacetoacetic acid ethyl ester, 2'-cyclopentyl-benzylideneacetoacetic acid ethyl ester, 4'-cyclopentyl-benzylideneacetoacetic acid methyl ester, 5'-cyclohexylbenzylideneacetoacetic acid methyl ester, 4'-phenylbenzylideneacetoacetic acid ethyl ester, 2'-, 3'- or 4'-chloro/bromo/fluorobenzylideneacetoacetic acid ethyl ester, 2'-fluorobenzylideneacetoacetic acid methyl ester, 3'-chlorobenzylideneacetylacetone, 3'-chlorobenzylidenepropionylacetic acid ethyl ester, 3'-chlorobenzylideneacetoacetic acid ethyl ester, 2'-chlorobenzylideneacetoacetic acid allyl ester, 2'-, 3'- or 4'-trifluoromethylbenzylideneacetoacetic acid propyl ester, 2'-trifluoromethylbenzylideneacetoacetic acid isopropyl ester, 3'-trifluoromethylbenzylideneacetoacetic acid methyl ester, 2'-trifluoromethoxybenzylideneacetoacetic acid methyl ester, 4'-trifluoromethoxybenzylideneacetoacetic acid ethyl ester, 2'-carbethoxybenzylideneacetoacetic acid ethyl ester, 3'-carbomethoxybenzylideneacetoacetic acid methyl ester, 4'-carboisopropoxybenzylideneacetoacetic acid ethyl ester, 4'-carboisopropoxybenzylideneacetoacetic acid allyl ester, 4'-aminobenzylideneacetoacetic acid ethyl ester, 4'-n-butylaminobenzylideneacetoacetic acid ethyl ester, 4'-dimethylaminobenzylideneacetoacetic acid methyl ester, 4'-hydroxybenzylideneacetoacetic acid methyl ester, 4'-dimethylaminocarbonylbenzylideneacetoacetic acid ethyl ester, 2'-nitrobenzylideneacetoacetic acid β-(dimethylamino)-ethyl ester, 2'-nitrobenzylideneacetoacetic acid β-(N-methylpiperatinyl-1)-ethyl ester, 2'-nitrobenzylidenacetoacetic acid β-(α-pyridyl)-ethyl ester, 3'-nitro-4'-chlorobenzylideneacetylacetone, 3'-nitro-4'-chlorobenzylideneacetoacetic acid t-butyl ester, 3'-nitro-4'-chlorobenzylideneacetoacetic acid methyl ester, 2'-nitro-4'-methylbenzylideneacetoacetic acid ethyl ester, 2'-azidobenzylideneacetoacetic acid ethyl ester, 3'-azidobenzylideneacetylacetone, 2'-methylmercaptobenzylideneacetoacetic acid methyl ester, 2'-methylmercaptobenzylideneacetoacetic acid isopropyl ester, 2'-sulphinylmethylbenzylideneacetoacetic acid ethyl ester, 2'-sulphonylmethylacetoacetic acid allyl ester, 4-sulphonylmethylacetoacetic acid ethyl ester, (1'-naphthylidene)-acetoacetic acid methyl ester, (1'-naphthylidene)-acetoacetic acid ethyl ester, (2'-naphthylidene)-acetoacetic acid ethyl ester, (2'-quinolyl)-methylideneacetoacetic acid ethyl ester, (3'-quinolyl)-methylideneacetoacetic acid methyl ester, (4'-quinolyl)-methylideneacetoacetic acid ethyl ester, (8'-quinolyl)-methylideneacetoacetic acid ethyl ester, (1'-isoquinolyl)-methylideneacetoacetic acid methyl ester, (3'-isoquinolyl)-methylideneacetoacetic acid methyl ester, α-pyridylmethylideneacetoacetic acid methyl ester, α-pyridylmethylideneacetoacetic acid ethyl ester, α-pyridylmethylideneacetoacetic acid allyl ester, α-pyridylmethylideneacetoacetic acid cyclohexyl ester, β-pyridylmethylideneacetoacetic acid β-methoxyethyl ester, γ-pyridylmethylideneacetoacetic acid methyl ester, 6-methyl-α-pyridylmethylideneacetoacetic acid ethyl ester, 4',6'-dimethoxy-(5'-pyrimidyl)methylideneacetoacetic acid ethyl ester, (2'-thienyl)-methylideneacetoacetic acid ethyl ester, (2'-furyl)-methylideneacetoacetic acid allyl ester, (2'-pyrryl)-methylideneacetoacetic acid methyl ester, 3'-nitrobenzylidenepropionylacetic acid ethyl ester, α-pyridylmethylidenepropionylacetic acid methyl ester and α-pyridylmethylideneacetylacetone.

The enaminocarboxylic acid esters of Formula III are similarly known or can be prepared according to known methods; see e.g. A. C. Cope, J. Amer. Chem. Soc. 67, 1017 (1945). The following are typical examples: β-aminocrotonic acid benzyl ester, βmethylaminocrotonic acid benzyl ester, β-ethylaminocrotonic acid benzyl ester, β-(2-methoxyethylamino)-crotonic acid benzyl ester, β-amino-β-ethylacrylic acid benzyl ester, β-amino-β-isopropylacrylic acid benzyl ester, β-aminocrotonic acid 2-phenylethyl ester, β-aminocrotonic acid 1-phenyl-propyl-2 ester, β-aminocrotonic acid 2-phenyl-propyl-1 ester, β-aminocrotonic acid 2-phenoxy ethyl ester, β-aminocrotonic acid 2-(naphthyloxy-1)-ethyl ester, β-aminocrotonic acid 4-methylbenzyl ester, β-aminocrotonic acid 3-methylbenzyl ester, β-aminocrotonic acid 4-isopropylbenzyl ester, β-aminocrotonic acid 3,4-dimethylbenzyl ester, β-aminocrotonic acid 4-methoxybenzyl ester, β-aminocrotonic acid 3-methoxybenzyl ester, β-aminocrotonic acid 3,4-dimethoxybenzyl ester, β-aminocrotonic acid 3,4,5-trimethoxybenzyl ester, β-aminocrotonic acid 4-n-butoxybenzyl ester, β-aminocrotonic acid 4-chlorobenzyl ester, β-aminocrotonic acid 3-chlorobenzyl ester, β-aminocrotonic acid 2-chlorobenzyl ester, β-aminocrotonic acid 3,4-dichlorobenzyl ester, β-aminocrotonic acid 4-fluorobenzyl ester, β-aminocrotonic acid 4-bromobenzyl ester, β-aminocrotonic acid 4-bromo-3-chlorobenzyl ester, β-aminocrotonic acid 3,4,5-trichlorobenzyl ester, β-aminocrotonic acid 3-chloro-4-methylbenzyl ester, β-aminocrotonic acid 3-chloro-4-methoxybenzyl ester, β-aminocrotonic acid 4-trifluoromethylbenzyl ester, β-aminocrotonic acid 3-trifluoromethylbenzyl ester, β-aminocrotonic acid 3-chloro-4-trifluoromethylbenzyl ester, β-aminocrotonic acid 4-trifluoromethoxybenzyl ester, β-aminocrotonic acid 4-hydroxybenzyl ester, β-aminocrotonic acid 4-aminobenzyl ester, β-aminocrotonic acid 4-n-butylaminobenzyl ester, β-aminocrotonic acid 4-dimethylaminobenzyl ester, β-aminocrotonic acid 4-nitrobenzyl ester, β-aminocrotonic acid 4-cyanobenzyl ester, β-aminocrotonic acid 4-carbamoylbenzyl ester, β-aminocrotonic acid 4-sulphamoylbenzyl ester, β-aminocrotonic acid 3-chloro-4-sulphamoylbenzyl ester, β-aminocrotonic acid 4-methylthiobenzyl ester, β-aminocrotonic acid 4-methylsulphinylbenzyl ester and β-aminocrotonic acid 4-methylsulphonylbenzyl ester.

The amines of Formula IV are known and include ammonia, methylamine, n-propylamine, isopropylamine, n-butylamine, sec.-butylamine, isobutylamine and β-methoxyethylamine.

The β-ketocarboxylic acid esters of Formula V used as starting materials are also known or can be prepared according to known methods; see e.g., Houben-Weyl, Methoden der Organischen Chemie (Methods of Organic Chemistry), VII/4, 230 et seq. (1968). The following are typical examples: formylacetic acid benzyl ester, acetoacetic acid benzyl ester, n-propionylacetic acid benzyl ester, isopropionylacetic acid benzyl ester, acetoacetic acid 2-phenylethyl ester, acetoacetic acid 1-phenyl-propyl-2 ester, acetoacetic acid 2-phenylpropyl-1 ester, acetoacetic acid 2-phenoxyethyl ester, acetoacetic acid 2-(naphthyloxy-1)-ethyl ester, acetoacetic acid 4-methylbenzyl ester, acetoacetic acid 3-methylbenzyl ester, acetoacetic acid 4-isopropylbenzyl ester, acetoacetic acid 3,4-dimethyl ester, acetoacetic acid 4-methoxybenzyl ester, acetoacetic acid 3-methoxybenzyl ester, acetoacetic acid 3,4-dimethoxybenzyl ester, acetoacetic acid 3,4,5-trimethoxybenzyl ester, acetoacetic acid 4-n-butoxybenzyl ester, acetoacetic acid 4-chlorobenzyl ester, acetoacetic acid 3-chlorobenzyl ester, acetoacetic acid 2-chlorobenzyl ester, acetoacetic acid 3,4-dichlorobenzyl ester, acetoacetic acid 4-fluorobenzyl ester, acetoacetic acid 4-bromobenzyl ester, acetoacetic acid 4-bromo-3-chlorobenzyl ester, acetoacetic acid 3,4,5-trichlorobenzyl ester, acetoacetic acid 3-chloro-4-methylbenzyl ester, acetoacetic acid 3-chloro-4-methoxybenzyl ester, acetoacetic acid 4-trifluoromethylbenzyl ester, acetoacetic acid 3-trifluoromethylbenzyl ester, acetoacetic acid 3-chloro-4-trifluoromethylbenzyl ester, acetoacetic acid 4-trifluoromethoxybenzyl ester, acetoacetic acid 4-hydroxybenzyl ester, acetoacetic acid 4-aminobenzyl ester, acetoacetic acid 4-n-butylaminobenzyl ester, acetoacetic acid 4-dimethylaminobenzyl ester, acetoacetic acid 4-nitrobenzyl ester, acetoacetic acid 4-cyanobenzyl ester, acetoacetic acid 4-carbamoylbenzyl ester, acetoacetic acid 4-sulphamoylbenzyl ester, acetoacetic acid 3-chloro-4-sulphamoylbenzyl ester, acetoacetic acid 4-methylthiobenzyl ester, acetoacetic acid 4-methylsulphinylbenzyl ester and acetoacetic acid 4-methylsulphonylbenzyl ester.

The ylidene-β-ketocarboxylic acid esters of Formula VI are also known or can be prepared according to known methods; see e.g., Org. Reactions XV, 204 et seq. (1967). The following are examples: 2'-nitrobenzylideneacetoacetic acid benzyl ester, 3'-nitrobenzylideneacetoacetic acid benzyl ester, 2'-trifluoromethylbenzylideneacetoacetic acid benzyl ester, 2'- or 3'-cyanobenzylideneacetoacetic acid benzyl ester, 2'-, 3'- or 4'-methoxybenzylideneacetoacetic acid benzyl ester, 2'-, 3'- or 4'-methylbenzylideneacetoacetic acid benzyl ester, 2'-cyclopropylbenzylideneacetoacetic acid benzyl ester, 2'-, 3'- or 4'-chloro/bromo/fluorobenzylideneacetoacetic acid benzyl ester, 2'-trifluoromethoxybenzylideneacetoacetic acid benzyl ester, 4'-carbomethoxybenzylideneacetoacetic acid benzyl ester, 4'-dimethylaminobenzylideneacetoacetic acid benzyl ester, 2'-methylmercaptobenzylideneacetoacetic acid benzyl ester, 2'-methylsulphinylbenzylideneacetoacetic acid benzyl ester, 2'-methyl-sulphonylbenzylideneacetoacetic acid benzyl ester, 1'-naphthylideneacetoacetic acid benzyl ester, 2'-nitrobenzylideneacetoacetic acid 2-phenylethyl ester, 2'-nitrobenzylideneacetoacetic acid 2-phenoxyethyl ester, 2'-nitrobenzylideneacetoacetic acid 4-methylbenzyl ester, 3'-nitrobenzylideneacetoacetic acid 3,4-dimethylbenzyl ester, 3'-nitrobenzylideneacetoacetic acid 4-methoxybenzyl ester, 2'-nitrobenzylideneacetoacetic acid 3,4-dimethoxybenzyl ester, 2'-nitrobenzylideneacetoacetic acid 3,4,5-trimethoxybenzyl ester, 2'-nitrobenzylideneacetoacetic acid 4-chlorobenzyl ester, 3'-nitrobenzylideneacetoacetic acid 3-chlorobenzyl ester, 2'-nitrobenzylideneacetoacetic acid 3,4-dichlorobenzyl ester, 2'-nitrobenzylideneacetoacetic acid 4-fluorobenzyl ester, 2'-nitrobenzylideneacetoacetic acid 3-chloro-4-methylbenzyl ester, 2'-nitrobenzylideneacetoacetic acid 3-chloro-4-methoxybenzyl ester, 2'-nitrobenzylideneacetoacetic acid 4-trifluoromethylbenzyl ester, 2'-nitrobenzylideneacetoacetic acid 4-trifluoromethoxybenzyl ester, 2'-nitrobenzylideneacetoacetic acid 4-dimethylaminobenzyl ester, 2'-nitrobenzylideneacetoacetic acid 4-cyanobenzyl ester, 2'-nitrobenzylideneacetoacetic acid 4-carbamoylbenzyl ester, 2'-nitrobenzylideneacetoacetic acid 4-sulphamoylbenzyl ester, 2'-nitrobenzylideneacetoacetic acid 3-chloro-4-sulphamoylbenzyl ester, 2'-nitrobenzylideneacetoacetic acid 4-methylsulphonylbenzyl ester, (2'-quinolyl)-methylideneacetoacetic acid benzyl ester, (1'-isoquinolyl)-methylideneacetoacetic acid benzyl ester, α-pyridylmethylideneacetoacetic acid benzyl ester, β-pyridylmethylideneacetoacetic acid benzyl ester, γ-pyridylmethylideneacetoacetic acid benzyl ester, (2'-thenyl)-methylideneacetoacetic acid benzyl ester, (2'-furyl)-methylideneacetoacetic acid benzyl ester and 3'-nitrobenzylidenepropionylacetic acid benzyl ester.

The enamino compounds of Formula VII are known or can be prepared according to known methods; see e.g., A. C. Cope, J. Amer. Chem. Soc, 67, 1017 (1945). The following are examples: 2-aminopent-2-en-4-one, 2-methylaminopent-2-en-4-one, 3-aminohept-3-en-5-one, β-aminocrotonic acid methyl ester, β-methylaminocrotonic acid methyl ester, β-(2-methoxyethylamino)-crotonic acid methyl ester, β-aminocrotonic acid ethyl ester, β-aminocrotonic acid n-butyl ester, β-aminocrotonic acid isopropyl ester, β-aminocrotonic acid cyclopentyl ester, β-aminocrotonic acid allyl ester, β-aminocrotonic acid 2-methoxyethyl ester, β-aminocrotonic acid 2-dimethylaminoethyl ester, β-aminocrotonic acid 2-(N-benzyl-N-methylamino)-ethyl ester, β-aminocrotonic acid 2-(piperidinyl-1)ethyl ester, β-aminocrotonic acid 2-(N-methylpiperazinyl-1)ethyl ester and β-aminocrotonic acid 2-(α-pyridyl)-ethyl ester.

The β-dicarbonyl compounds of Formula VIII are known or can be prepared according to known methods; see e.g., Houben-Weyl, Methoden der Organischen Chemie (Methods of Organic Chemistry), VII/4, 230 et seq. (1968). The following are examples: 2,4-pentanedione, 3,5-heptanedione, 2,6-nonanedione, 2,6-dimethyl-3,5-heptanedione, formylacetic acid ethyl ester, acetoacetic acid methyl ester, acetoacetic acid ethyl ester, acetoacetic acid n-butyl ester, acetoacetic acid isopropyl ester, acetoacetic acid cyclopentyl ester, acetoacetic acid alkyl ester, acetoacetic acid propargyl ester, acetoacetic acid 2-methoxyethyl ester, acetoacetic acid 2-dimethylaminoethyl ester, acetoacetic acid 2-(piperidinyl-1)-ethyl ester, acetoacetic acid 2-(α-pyridyl)-ethyl ester, propionylacetic acid ethyl ester, butyrylacetic acid methyl ester and isobutyrylacetic acid ethyl ester.

The aldehydes of Formula IX are known or can be prepared according to known methods; see e.g., E. Mosettig, Org. Reactions, VIII, 218 et seq. (1954). The following are examples: benzaldehyde, 4-phenylbenzaldehyde, 2-, 3- or 4-methylbenzaldehyde, 2- or 4-n-butylbenzyldehyde, 2-, 3- or 4-isopropylbenzaldehyde, 2- or 4-cyclopropylbenzaldehyde, 2-vinylbenzaldehyde, 2-ethinylbenzaldehyde, 2-, 3- or 4-methoxybenzaldehyde, 2-, 3- or 4-chloro/bromo/fluorobenzaldehyde, 2-, 3- or 4-trifluoromethylbenzaldehyde, 2-, 3- or 4-trifluoromethoxybenzaldehyde, 4-hydroxybenzaldehyde, 2-, 3- or 4-nitrobenzaldehyde, 2-, 3- or 4-cyanobenzaldehyde, 3-azidobenzaldehyde, 2-, 3- or 4-dimethylaminobenzaldehyde, 3-carbethoxybenzaldehyde, 3- or 4-carbamoylbenzaldehyde, 2-, 3- or 4-methylmercaptobenzaldehyde, 2-, 3- or 4-methylsulphinylbenzaldehyde, 2-, 3- or 4-methylsulphonylbenzaldehyde, 3,4,5-trimethoxybenzaldehyde, 2,3- or 2,6-dichlorobenzaldehyde, 2,4-dimethylbenzaldehyde, 2,4- or 2,6-dinitrobenzaldehyde, 2-chloro-6-nitrobenzaldehyde, 4-chloro-2-nitrobenzaldehyde, 2-nitro-4-methoxybenzaldehyde, 2-nitro-4-cyanobenzaldehyde, 2-chloro-4-cyano-benzaldehyde, 4-cyano-2-methylbenzaldehyde, 3-methyl-4-trifluoromethylbenzaldehyde, 3-chloro-4-trifluoromethylbenzaldehyde, 4-chloro-3-sulphamoylbenzaldehyde, α-, β- or γ-pyridinaldehyde, 6-methylpyridin-2-aldehyde, furan-2-aldehyde, thiophen-2-aldehyde, pyrrol-2-aldehyde, pyrimidin-4-aldehyde, 5-nitro-6-methyl-pyridin-2-aldehyde, quinolin-2-aldehyde, isoquinolin-1-aldehyde and 1- or 2-naphthaldehyde.

Diluents which can be used in the process are water and all inert organic solvents including alcohols, especially alkanols such as ethanol, methanol and isopropanol, ethers such as dioxane, diethyl ether, tetrahydrofuran, glycol monomethyl ether and glycol dimethyl ether, glacial acetic acid, dimethylformamide, dimethylsulfoxide, acetonitrile, pyridine and the like. Reaction temperatures can be varied within a substantial range. In general, the reaction is carried out at temperatures of from about 20° C to about 150° C, but advantageously at the boiling point of the particular solvent. The reaction can be carried out under elevated pressure but in general, normal pressure is employed. The amines of Formula IV are generally used in a 1 to 2 molar excess. All other reactants are generally employed in substantially equimolar amounts.

In addition to the compounds for which typical methods of preparation are presented hereafter, the following compounds of the present invention are specifically noted: 2,6-dimethyl-4-(2-methylphenyl)-1,4-dihydropyridine-3-methoxycarbonyl-5-carboxylic acid benzyl ester, 2,6-dimethyl-4-(3-isopropylphenyl)-1,4-dihydropyridine-3-methoxycarbonyl-5-carboxylic acid benzyl ester, 2,6-dimethyl-4-(2-cyclopropylphenyl)-1,4-dihydropyridine-3-methoxycarbonyl-5-carboxylic acid benzyl ester, 2,6-dimethyl-4-(2-ethinylphenyl)-1,4-dihydropyridine-3-methoxycarbonyl-5-carboxylic acid benzyl ester, 2,6-dimethyl-4-(2-methoxyphenyl)-1,4-dihydropyridine-3-ethoxycarbonyl-5-carboxylic acid benzyl ester, 2,6-dimethyl-4-(3-methoxyphenyl)-1,4-dihydropyridine-3-ethoxycarbonyl-5-carboxylic acid benzyl ester, 2,6-dimethyl-4-(3,4,5-trimethoxyphenyl)-1,4-hydropyridine-3-methoxycarbonyl-5-carboxylic acid benzyl ester, 2,6-dimethyl-4-(2-fluoropheyl)-1,4-dihydropyridine-3-methoxycarbonyl-5-carboxylic acid benzyl ester, 2,6-dimethyl-4-(3-trifluoromethylphenyl)-1,4-dihydropyridine-3-methoxycarbonyl-5-carboxylic acid benzyl ester, 2,6-dimethyl-4-(4-trifluoromethylphenyl)-1,4-dihydropyridine-3-methoxycarbonyl-5-carboxylic acid benzyl ester, 2,6-dimethyl-4-(2-trifluoromethoxyphenyl)-1,4-dihydropyridine-3-methoxycarbonyl-5-carboxylic acid benzyl ester, 2,6-dimethyl-4-(2-cyanophenyl)-1,4-dihydropyridine-3-ethoxycarbonyl-5-carboxylic acid benzyl ester, 2,6-dimethyl-4-(3-cyanophenyl)-1,4-dihydropyridine-3-isopropoxycarbonyl-5-carboxylic acid benzyl ester, 2,6-dimethyl-4-(3-azidophenyl)-1,4-dihydropyridine-3-methoxycarbonyl-5-carboxylic acid benzyl ester, 2,6-dimethyl-4-(4-dimethylaminophenyl)-1,4-dihydropyridine-3-methoxycarbonyl-5-carboxylic acid benzyl ester, 2,6-dimethyl-4-(3-sulphamoylphenyl)-1,4-dihydropyridine-3-methoxycarbonyl-5-carboxylic acid benzyl ester, 2,6-dimethyl-4-(4-chloro-3-sulphamoylphenyl)-1,4-dihydropyridine-3-ethoxycarbonyl-5-carboxylic acid ester, 2,6-dimethyl-4-(2-methylmercaptophenyl)-1,4-dihydropyridine-3-methoxycarbonyl-5-carboxylic acid benzyl ester, 2,6-dimethyl-4-(2-methylsulphinylphenyl)-1,4-dihydropyridine-3-ethoxycarbonyl-5-carboxylic acid benzyl ester, 2,6-dimethyl-4-(2-methylsulphonylphenyl)-1,4-dihydropyridine-3-ethoxycarbonyl-5-carboxylic acid benzyl ester, 2,6-dimethyl-4-(2-methylphenyl)-1,4-dihydropyridine-3-isoproxycarbonyl-5-carboxylic acid 4-methoxybenzyl ester, 2,6-dimethyl-4(2-cyclopropylphenyl)-1,4-dihydropyridine-3-ethoxycarbonyl-5-carboxylic acid 4-methylbenzyl ester, 2,6-dimethyl-4-(2-methoxyphenyl)-1,4-dihydropyridine-3-(β-methoxyethyl)-carbonyl-5-carboxylic a acid 4-chlorobenzyl ester, 2,6-dimethyl 4-(3-trifluoromethylphenyl)-1,4-dihydropyridine-3-methoxycarbonyl-5-carboxylic acid 3,4-dichlorobenzyl ester, 2,6-dimethyl-4-(2-trifluoromethoxyphenyl)-1,4-dihydropyridine-3-methoxycarbonyl-5-carboxylic acid 2-phenylethyl ester, 2,6-dimethyl-4-(2-trifluoromethoxyphenyl)-1,4-dihydropyridine-3-methoxycarbonyl-5-carboxylic acid 2-phenoxyethyl ester, 2,6-dimethyl-4-(2-cyanophenyl)-1,4-dihydropyridine-3-methoxycarbonyl-5-carboxylic acid 2-phenylether ester, 2,6-dimethyl-4-(2-cyanophenyl)-1,4-dihydropyridine-3-methoxycarbonyl-5-carboxylic acid 3,4,5-trimethoxybenzyl ester, 2,6-dimethyl-4-(isoquinolyl)-1,4-dihydropyridine-3-methoxycarbonyl-5-carboxylic acid benzyl ester and 2,6-dimethyl-4-(quinolyl-2)-1,4-dihydropyridine-3-methoxycarbonyl-5-carboxylic acid 2-phenyl-ethyl ester.

Compound according to the invention which are of particular interest are those of Formula I in which R is phenyl, unsubstituted or substituted by nitro. cyano, trifluoromethyl or halo, or R is pyridyl;

$R^1$ is alkyl or alkoxy, each with 1 to 4 carbon atoms, or the group —$OR^6$ wherein $R^6$ is alkoxyalkyl of up to 4 carbon atoms or cycloalkyl of 5 or 6 carbon atoms;

$R^2$ and $R^4$ are the same or different and are ethyl or methyl;

$R^3$ is hydrogen or lower alkyl;

X is alkylene of 1 to 4 carbon atoms optionally branched; and $R^5$ is phenoxy or phenyl optionally substituted by 1, 2 or 3 identical or different substituents selected from the group consisting of alkyl and alkoxy, each with 1 to 4 carbon atoms, halo, trifluoromethyl and nitro.

When either R or $R^5$ is polysubstituted, it will be appreciated that the patterns of substitution include only those which are sterically permissible.

The new compounds can be used as medicaments and have a broad and diverse spectrum of pharmacological action. In particular the following main actions are conveniently demonstrable in animal models;

1. On parenteral, oral and perlingual administration, the compounds produce a distinct and long-lasting dilation of th coronary vessels. This action on the coronary vessels is intensified by a simultaneous nitrite-like effect of reducing the load on the heart. Heart metabolism is thus influenced or modified in the sense of an energy saving.

2. The excitability of the stimulus formation and excitation conduction system within the heart is lowered, so that an anti-fibrillation action at therapeutic doses results.

3. The tone of the smooth muscle of the vessels is greatly reduced under the action of the compounds. This vascular-spasmolytic action can take place in the entire vascular system or can manifest itself more or less isolated in circumscribed vascular regions, such as, for example, the central nervous system.

4. The compounds lower and blood pressure of normotonic and hypertonic animals and can thus be used as anti-hypertensive or hypotensive agents.

5. The compounds have strong muscular-spasmolytic actions which manifest themselves on the smooth muscle of the stomach, the intestinal tract, the urogenital tract and the respiratory system.

In general, a satisfactory pharmacological response is observed, in the case of intravenous administration, upon administration of from about 0.0001 to about 1 mg/kg, preferably 0.0005 to 0.1 mg/kg, of body weight daily. In the case of oral administration, the dosage is from 0.005 to 10 mg/kg, preferably 0.05 to 5 mg/kg, of body weight daily.

At times, it may of course be necessary to deviate from these ranges mentioned and in particular to do so as a function of body weight, the route of administration, the species, its response towards the medicine and its overall condition, and the time or interval at which it is administered. In some cases, less than the above-mentioned minimum amount produces an adequate response while in other cases the upper limited mentioned must be exceeded. When large amounts are administered, it is often advisable to divide these into several administrations over the course of the day.

The hypotensive activity of these compounds can be seen from the following in which are presented the limiting doses, in mg/kg, at which various compounds have a discernable hypotensive effect on the hypertonic rat.

| Compound | Dose (mg/kg) |
|---|---|
| 2,6-dimethyl-3-carbomethoxy-4-(2-nitrophenyl)-1,4-dihydropyridine-5-carboxylic acid benzyl ester | 0.3 |
| 2,6-dimethyl-3-carbomethoxy-4-(2-nitrophenyl)-1,4-dihydropyridine-5-carboxylic acid 4-chlorobenzyl ester | 1.0 |
| 2,6-dimethyl-3-carbomethoxy-4-(2-nitrophenyl)-1,4-dihydropyridine-5-carboxylic acid 3,4-dichlorobenzyl ester | 1.0 |
| 2,6-dimethyl-3-carbomethoxy-4-(2-nitrophenyl)-1,4-dihydropyridine-5-carboxylic acid 4-methylbenzyl ester | 1.0 |
| 2,6-dimethyl-3-carbisopropoxy-4-(3-nitrophenyl)-1,4-dihydropyridine-5-carboxylic acid benzyl ester | 3.1 |
| 2,6-dimethyl-3-carbisopropoxy-4-(3-nitrophenyl)-1,4-dihydropyridine-5-carboxylic acid 4-chlorobenzyl ester | 10.0 |
| 2,6-dimethyl-3-carbisopropoxy-4-(3-nitrophenyl)-1,4-dihydropyridine-5-carboxylic acid 3,4-dichlorobenzyl ester | 3.1 |
| 2,6-dimethyl-3-carbisopropoxy-4-(3-nitrophenyl)-1,4-dihydropyridine-5-carboxylic acid 2-chlorobenzyl ester | 10.0 |
| 2,6-dimethyl-3-carbo(2-methoxyethoxy)-4-(3-nitrophenyl)-1,4-dihydropyridine-5-carboxylic acid benzyl ester | 10.0 |
| 2,6-dimethyl-3-carbo(2-methoxyethoxy)-4-(3-nitrophenyl)-1,4-dihydropyridine-5-carboxylic acid 1-phenylethyl ester | 1.0 |
| 2,6-dimethyl-3-carbo(2-methoxyethoxy)-4-(3-nitrophenyl)-1,4-dihydropyridine-5-carboxylic acid 1-(4-chlorophenyl)-ethyl ester | 0.3 |

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g. a teaspoonful, contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle in which it is insoluble.

Fluid unit dosage forms for parenteral administration can be prepared by suspending or dissolving a measured amount of the compound in a nontoxic liquid vehicle suitable for injection such as an aqueous or oleaginous medium and sterilizing the suspension or solution. Alternatively a measured amount of the compound is placed in a vial amd the vial and its contents are sterilized and sealed. An accompanying vial or vehicle can be provided for mixing prior to administration.

The following examples will serve to further typify the present invention, in particular the manner of synthesizing these compounds, but should not be contrued as a restriction on the scope of the invention, the invention being defined solely by the appended claims.

EXAMPLES 1 TO 6

2,6-Dimethyl-3-methoxycarbonyl-4-(2'-nitrophenyl)-1,4-dihydropyridine-5-carboxylic acid benzyl ester

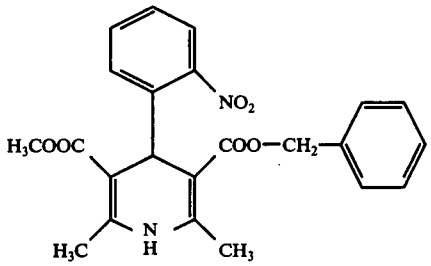

EXAMPLE 1

18.7 g (75 mmols) of 2'-nitrobenzylideneacetoacetic acid methyl ester and 14.3 g 75 mmols) of β-aminocrotonic acid benzyl ester in 120 ml of ethanol were together heated for 10 hours under reflux. After the reaction mixture had cooled, the solvent was distilled off in vacuo and 50 ml of a 2:1 mixture of ether and petroleum ether were added to the oily residue. The product crystallised throughout after a short time and was filtered off and recrystallised from ethanol.

Melting point: 136° C. Yield: 22.2 g (70%)

EXAMPLE 2

18.7 g (75 mmols) of 2'-nitrobenzylideneacetoacetic acid methyl ester, 14.4 g (75 mmols) of acetoacetic acid benzyl ester and 9 ml (132 mmols) of a 25 percent strength aqueous solution of ammonia, in 120 ml of ethanol, were together heated for 15 hours under reflux.

Thereafter the solvent was distilled off in vacuo, and the residue was triturated with 30 ml of diethyl ether, filtered off and recrystallised from ethanol.

Melting point: 135°–136° C. Yield: 18.3 g (58%).

EXAMPLE 3

16.3 (50 mmols) of 2'-nitrobenzylideneacetoacetic acid benzyl ester and 5.8 g (50 mmols) of β-aminocrotonic acid methyl ester in 90 ml of ethanol were together heated for 10 hours under reflux. After the reaction mixture had cooled, the solvent was distilled off in vacuo. The oily residue crystallised throughout on cooling with ice and was filtered off and recrystallised from ethanol. Melting point: 136° C. Yield: 14.2 g (67%).

EXAMPLE 4

16.3 g (50 mmols) of 2'-nitrobenzylideneacetoacetic acid benzyl ester, 5.8 g (50 mmols) of acetoacetic acid methyl ester and 6 ml (88 mmols) of a 25 per cent strength aqueous ammonia solution, in 90 ml of methanol, were together heated for 15 hours under reflux. Thereafter the solvent was distilled off in vacuo and the oily residue was mixed with a little ether, whereupon the product soon crystallised. The solid substance was filtered off and recrystallised from ethanol.

Melting point: 136° C. Yield 13 g (62%).

EXAMPLE 5

9.6 g (50 mmols) of β-aminocrotonic acid benzyl ester, 7.5 g (50 mmols) of 2-nitrobenzaldehyde and 5.8 g (50 mmols) of acetoacetic acid methyl ester in 90 ml of methanol were together heated for 15 hours under reflux. After the reaction mixture had cooled the solvent was distilled off and the oily residue was mixed with ether and cooled with ice. Hereupon, the product soon crystallised and was filtered off and recrystallised from ethanol.

Melting point: 136° C. Yield: 10.8 g (51%).

EXAMPLE 6

5.8 g (50 mmols) of β-aminocrotonic acid methyl ester, 7.5 g (50 mmols) of 2-nitrobenzaldehyde and 9.6 g (50 mmols) of acetoacetic acid benzyl ester in 90 ml of ethanol were together heated for 15 hours under reflux. Thereafter the solvent was distilled off in vacuo and the residue was triturated with 30 ml of diethyl ether whilst cooling with ice, filtered off and recrystallised from ethanol. Melting point: 135°–136° C. Yield: 9 g (43%).

EXAMPLES 7 TO 12

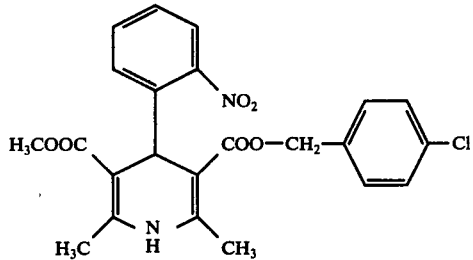

EXAMPLE 7

Analogously to Example 1, heating a solution of 75 mmols of 2'-nitrobenzylideneacetoacetic acid methyl ester and 75 mmols of β-aminocrotonic acid 4-chlorobenzyl ester in 120 ml of ethanol for 10 hours gave 2,6-dimethyl-3-methyoxycarbonyl-4-(2'-nitrophenyl)-1,4-dihydropyridine-5-carboxylic acid 4-chlorobenzyl ester of melting point 129° C (from ethanol).

Yield: 67%

EXAMPLE 8

The compound of Example 7 was also obtained analogously to Example 2 by heating a solution of 75 mmols of 2'-nitrobenzylideneacetoacetic acid methyl ester, 75 mmols of acetoacetic acid 4-chlorobenzyl ester and 9 ml of concentrated ammonia in 120 ml of ethanol.

Yield 55% of theory.

EXAMPLE 9

The compound of Example 7 was also obtained analogously to Example 3 by heating a solution of 50 mmols of 2'-nitrobenzylideneacetoacetic acid 4-chlorobenzyl ester and 50 mmols of β-aminocrotonic acid methyl ester in 90 ml of methanol.

Yield: 62% of theory.

EXAMPLE 10

The compound of Example 7 was also obtained analogously to Example 4 by heating a solution of 50 mmols of 2'-nitrobenzylideneacetoacetic acid 4-chlorobenzyl ester, 50 mmols of acetoacetic acid methyl ester and 6 ml of concentrated ammonia in 90 ml of methanol.

Yield: 55% of theory.

EXAMPLE 11

The compound of Example 7 was also obtained analogously to Example 5 by heating a solution of 50 mmols of β-aminocrotonic acid 4-chlorobenzyl ester, 50 mmols of 2-nitrobenzaldehyde and 50 mmols of acetoacetic acid methyl ester in 90 ml of methanol.

Yield: 60% of theory.

EXAMPLE 12.

The compound of Example 7 was also obtained analogously to Example 6 by heating a solution of 50 mmols of β-aminocrotonic acid methyl ester, 50 mmols of 2-nitrobenzaldehyde and 50 mmols of acetoacetic acid 4-chlorobenzyl ester in 90 ml of ethanol.

Yield: 45% of theory.

EXAMPLES 13 TO 18

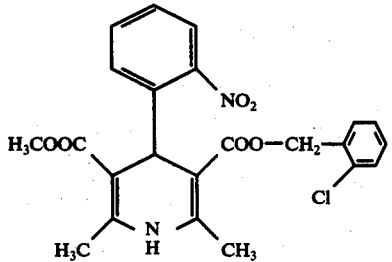

EXAMPLE 13

Analogously to Example 1 heating a solution of 75 mmols of 2'-nitrobenzylideneacetoacetic acid methyl ester and 75 mmols of β-aminocrotonic acid 2-chlorobenzyl ester in 120 ml of ethanol also gave 2,6-dimethyl-3-methoxycarbonyl-4-(2'-nitrophenyl)-1,4-dihydropyridine-5-carboxylic acid 2-chloro-benzyl ester of melting point 147° C (from ethanol).

Yield: 55% of theory.

EXAMPLE 14

The compound of Example 13 was also obtained analogously to Example 2 by heating a solution of 75 mmols of 2'-nitrobenzylideneacetoacetic acid methyl ester, 75 mmols of acetoacetic acid 2-chlorobenzyl ester and 9 ml of concentrated ammonia in 120 ml of ethanol.

Yield: 48% of theory.

EXAMPLE 15

The compound of Example 13 was also contained analogously to Example 3 by heating a solution of 50 mmols of 2'-nitrobenzylideneacetoacetic acid 2-chlorobenzyl ester and 50 mmols of β-aminocrotonic acid methyl ester in 90 ml of methanol.

Yield: 60% of theory.

EXAMPLE 16

The compound of Example 13 was also obtained analogously to Example 4 by heating a solution of 50 mmols of 2'-nitrobenzylideneacetoacetic acid 2-chlorobenzyl ester, 50 mmols of acetoacetic acid methyl ester and 6 ml of concentrated ammonia in 90 ml of methanol.

EXAMPLE 17

The compound of Example 13 was also obtained analogously to Example 5 by heating a solution of 50 mmols of β-amino crotonic acid 2-chlorobenzyl ester, 50 mmols of 2-nitrobenzaldehyde and 50 mmols of acetoacetic acid methyl ester in 90 ml of methanol.

Yield: 45% of theory.

EXAMPLE 18

The compound of Example 13 was also obtained analogously to Example 6 by heating a solution of 50 mmols of β-aminocrotonic acid methyl ester, 50 mmols of 2-nitrobenzaldehyde and 50 mmols of acetoacetic acid 2-chlorobenzyl ester in 90 ml of ethanol.

Yield 42% of theory.

EXAMPLES 19 TO 24

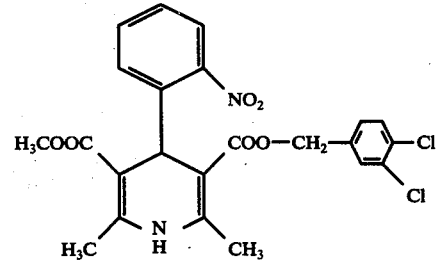

EXAMPLE 19

Analogously to Example 1 heating a solution of 75 mmols of 2'-nitrobenzylideneacetoacetic acid methyl ester and 75 mmols of β-aminocrotonic acid 3,4-dichlorobenzyl ester in 120 ml of n-propanol gave 2,6-dimethyl-3-methoxycarbonyl-4-(2'-nitrophenyl)-1,4-dihydropyridine-5-carboxylic acid 3,4-dichlorobenzyl ester of melting point 137° C (from ethanol).

Yield: 75% of theory.

EXAMPLE 20

The compound of Example 19 was also obtained analogously to Example 2 by heating a solution of 75 mmols of 2'-nitrobenzylideneacetoacetic acid methyl ester, 75 mmols of acetoacetic acid 3,4-dichlorobenzyl ester and 9 ml of concentrated ammonia in 120 ml of ethanol.

Yield: 65% of theory.

EXAMPLE 21

The compound of Example 19 was also obtained analogously to Example 3 by heating a solution of 50 mmols of 2'-nitrobenzylideneacetoacetic acid 3,4-dichlorobenzyl ester and 50 mmols of β-aminocrotonic acid methyl ester in 90 ml of n-propanol.

Yield: 72% of theory.

EXAMPLE 22

The compound of Example 19 was also obtained analogously to Example 4 by heating a solution of 50 mmols of 2'-nitrobenzylideneacetoacetic acid 3,4-dichlorobenzyl ester, 50 mmols of acetoacetic acid methyl ester and 6 ml of concentrated ammonia in 90 ml of ethanol.

Yield: 60% of theory.

EXAMPLE 23

The compound of Example 19 was also obtained analogously to Example 5 by heating a solution of 50 mmols of β-aminocrotonic acid 3,4-dichlorobenzyl ester, 50 mmols of 2-nitrobenzaldehyde and 50 mmols of acetoacetic acid methyl ester in 90 ml of n-propanol.

Yield- 48. of theory.

EXAMPLE 24

The compound of Example 19 was also obtained analogously to Example 6 by heating a solution of 50 mols of β-aminocrotonic acid methyl ester, 50 mmols of 2-nitrobenzaldehyde and 50 mmols of acetoacetic acid 3,4-dichlorobenzyl ester in 90 ml of ethanol.

Yield: 52% of theory.

EXAMPLES 25 TO 30

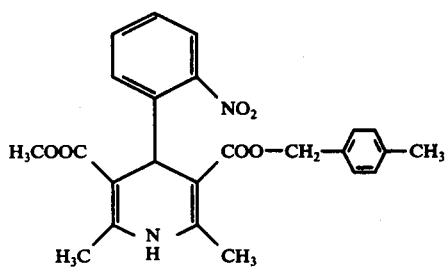

EXAMPLE 25

Analogously to Example 1, heating a solution of 75 mmols of 2'-nitrobenzylideneacetoacetic acid methyl ester and 75 mmols of β-aminocrotonic acid 4 methylbenzyl ester in 120 ml of dimethylformamide for 5 hours gave 2,6-dimethyl-3-methoxycarbon 1-4-(2'-nitrophenyl)-1,4-dihydropyridine-5-carboxylic acid 4-methylbenzyl ester of melting point 126° C (from ethanol).

Yield: 72% of theory.

EXAMPLE 26

The compound of Example 25 was also obtained analogously to Example 2 by heating a solution of 75 mmols of 2'-nitrobenzylideneacetoacetic acid methyl ester, 75 mmols of acetoacetic acid 4-methylbenzyl ester and 9 ml of concentrated ammonia in 120 ml of ethanol.

Yield- 64% of theory.

EXAMPLE 27

The compound of Example 25 was also obtained analogously to Example 3 by heating a solution of 50 mmols of 2'-nitrobenzylideneacetoacetic acid 4-methylbenzyl ester and 50 mmols of β-aminocrotonic acid methyl ester in 90 ml of dimethylformamide.

Yield: 65% of theory.

EXAMPLE 28

The compound of Example 25 was also obtained analogously to Example 4 by heating a solution of 50 mmols of 2'-nitrobenzylideneacetoacetic acid 4-methylbenzyl ester, 50 mmols of acetoacetic acid methyl ester and 6 ml of concentrated ammonia in 90 ml of ethanol.

Yield: 59% of theory.

EXAMPLE 29

The compound of Example 25 was also obtained analogously to Example 5 by heating a solution of 50 mmols of β-aminocrotonic acid 4 methylbenzyl ester, 50 mmols of 2-nitrobenzaldehyde and 50 mmols of acetoacetic acid methyl ester in 90 ml of n-propanol.

Yield- 55% of theory.

EXAMPLE 30

The compound of Example 25 was also obtained analogously to Example 6 by heating a solution of 50 mmols of β-aminocrotonic acid methyl ester, 50 mmols of 2-nitrobenzaldehyde and 50 mmols of acetoacetic acid 4-methylbenzyl ester in 90 ml of n-propanol.

Yield: 62% of theory.

EXAMPLES 31 TO 36

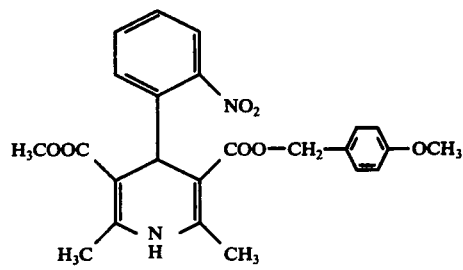

EXAMPLE 31

Analogously to Example 1, heating a solution of 75 mmols of 2'-nitrobenzylideneacetoacetic acid methyl ester and 75 mmols of β-aminocrotonic acid 4-methoxybenzyl ester in 120 ml of n-butanol for 7 hours gave 2,6-dimethyl-3methoxycarbonyl-4-(2'-nitrophenyl)-1,4-dihydropyridine-5-carboxylic acid 4-methoxybenzyl ester of melting point 152° C (from ethanol).

Yield: 75. of theory.

EXAMPLE 32

The compound of Example 31 'was also obtained analogously to Example 2 by heating a solution of 75 mmols of 2'-nitrobenzylideneacetoacetic acid methyl ester, 75 mmols of acetoacetic acid 4-methoxybenzyl ester and 9 ml of concentrated ammonia in 120 ml of ethanol.

Yield: 61% of theory.

EXAMPLE 33

The compound of Example 31 was also obtained analogously to Example 3 by heating a solution of 50 mmols of 2'-nitrobenzylideneacetoacetic acid 4-methoxybenzyl ester and 50 mmols of β-aminocrotonic acid methyl ester in 90 ml of n-butanol. Yield: 67% of theory.

EXAMPLE 34

The compound of Example 31 was also obtained analogously to Example 4 by heating a solution of 50 mmols of 2'-nitrobenzylideneacetoacetic acid 4-methoxybenzyl ester, 50 mmols of acetoacetic acid methyl ester and 6 ml of concentrated ammonia in 90 ml of n-propanol.
Yield: 58. of theory.

EXAMPLE 35

The compound of Example 31 as also obtained analogously to Example 5 by heating a solution of 50 mmols of β-aminocrotonic acid 4-methoxybenzyl ester, 50 mmols of 2-nitrobenzaldehyde and 50 mmols of acetoacetic acid methyl ester in 90 ml of n-propanol.
Yield: 62% of theory.

EXAMPLE 36

The compound of Example 31 was also obtained analogously to Example 6 by heating a solution of 50 mmols of β-aminocrontic acid methyl ester, 50 mmols of 2-nitrobenzaldehyde and 50 mmols of acetoacetic acid 4-methoxybenzyl ester in 90 ml of n-propanol.
Yield: 67% of theory.

EXAMPLES 37 TO 42

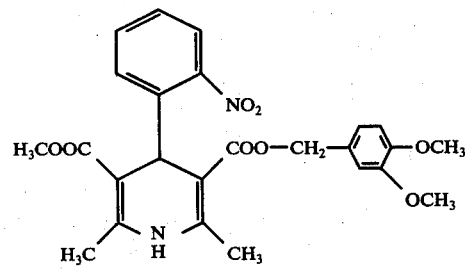

EXAMPLE 37

Analogously to Example 1 heating a solution of 65 mmols of 2'-nitrobenzylideneacetoacetic acid methyl ester and 75 mmols of β-aminocrotonic acid 3,4-dimethoxybenzyl ester in 120 ml of glycol monomethyl ether for 5 hours gave 2,6-dimethyl-3-methoxycarbonyl-4-(2'-nitrophenyl)-1,4-dihydropyridine-5-carboxylic acid 3,4-dimethoxybenzyl ester of melting point 149° C (from methanol).
Yield: 77% of theory.

EXAMPLE 38

The compound of Example 37 was also obtained analogously to Example 2 by heating a solution of 75 mmols of 2'-nitrobenzylideneacetoacetic acid methyl ester, 75 mmols of acetoacetic acid 3,4-dimethoxybenzyl ester and 9 ml of concentrated ammonia in 120 ml of n-propanol.
Yield: 65% of theory.

EXAMPLE 39

The compound of Example 37 was also obtained analogously to Example 3 by heating a solution of 50 mmols of 2'-nitrobenzylideneacetoacetic acid 3,4-dimethoxybenzyl ester and 50 mmols of β-aminocrotonic acid methyl ester in 90 ml of glycol monomethyl ether.
Yield: 71% of theory. Example 40

The compound of Example 37 was also obtained analogously to Example 4 by heating a solution of 50 mmols of 2'-nitrobenxylideneacetoacetic acid 3,4-dimethoxybenzyl ester, 50 mmols of acetoacetic acid methyl ester and 6 ml of concentrated ammonia in 90 ml of n-propanol.
Yield: 62% of theory.

EXAMPLE 41

The compound of Example 37 was also obtained analogously to Example 5 by heating a solution of 50 mmole of β-aminocrotonic acid 3,4-dimethoxybenzyl ester, 50 mmols of 2-nitro benzaldehyde and 50 mmols of acetoacetic methyl ester in 90 ml of n-propanol.
Yield: 73% of theory.

Example 42

The compound of Example 37 was also obtained analogously to Example 6 by heating a solution of 50 mmols of β-aminocrontonic acid methyl ester, 50 mmols of 2-nitrobenzaldehyde and 50 mmols of acetoacetic acid 3,4-dimethoxybenzyl ester in 90 ml of n-propanol.
Yield: 68% of theory.

EXAMPLES 43 to 48

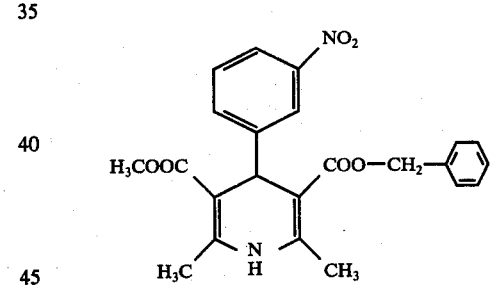

EXAMPLE 43

Analogously to Example 1 heating a solution of 75 mmols of 3'-nitrobenzylideneacetoacetic acid methyl ester and 75 mmols of β-aminocrotonic acid benzyl ester in 120 ml of pyridine for 10 hours gave 2,6-dimethyl-3-methoxycarbonyl-4-(3'-nitrophenyl)-1,4-dihydropyridine-5-carboxylic acid benzyl ester of melting point 133° C (from ethanol).
Yield: 75% of theory.

EXAMPLE 44

The compound of Example 43 was obtained analogously to Example 2 by heating a solution of 75 mmols of 3'-nitrobenzylideneacetoacetic acid methyl ester, 75 mmols of acetoacetic acid benzyl ester and 9 ml of concentrated ammonia in 120 ml of ethanol.
Yield: 66% of theory.

EXAMPLE 45

The compound of Example 43 was also obtained analogously to Example 3 by heating a solution of 50 mmols of 3'-nitrobenzylideneacetoacetic acid benzyl ester and 50 mmols of β-aminocrotonic acid methyl ester in 90 ml of pyridine.
Yield 77% of theory.

EXAMPLE 46

The compound of Example 43 was also obtained analogously to Example 4 by heating a solution of 50 mmols of 3'-nitrobenzylideneacetoacetic acid benzyl ester, 50 mmols of acetoacetic acid methyl ester and 6 ml of concentrated ammonia in 90 ml of n-propanol.
Yield: 70% of theory.

EXAMPLE 47

The compound of Example 43 was also obtained analogously to Example 5 by heating a solution of 50 mmols of β-aminocrotonic acid benzyl ester, 50 mmols of 3-nitrobenzaldehyde and 50 mmols of acetoacetic acid methyl ester in 90 ml of n-propanol.
Yield: 64% of theory.

EXAMPLE 48

The compound of Example 43 was also obtained analogously to Example 6 by heating a solution of 50 mmols of β-aminocrotonic acid methyl ester, 50 mmols of 3-nitrobenzaldehyde and 50 mmols of acetoacetic acid benzyl ester on 90 ml of ethanol.
Yield: 69% of theory.

EXAMPLE 49 to 54

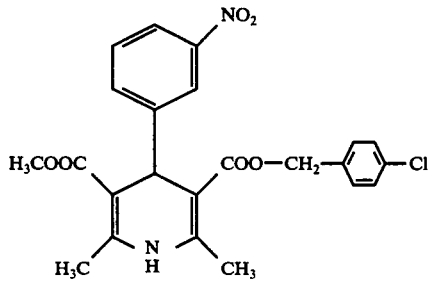

EXAMPLE 49

Analogously to Example 1 heating a solution of 75 mmols of 3'-nitrobenzylideneacetoacetic acid methyl ester and 75 mmols of β-aminocrotonic acid 4-chlorobenzyl ester in 120 ml of ethanol gave 2,6-dimethyl-3-methoxycarbonyl-4-(3'-nitrophenyl)-1,4-dihydropyridine-5-carboxylic acid 4-chlorobenzyl ester of melting point 169° C (from ethanol).
Yield: 72% of theory.

EXAMPLE 50

The compound of Example 49 was also obtained analogously to Example 2 by heating a solution of 75 mmols of 3'-nitrobenzylideneacetoacetic acid methyl ester, 75 mmols of acetoacetic acid 4-chlorobenzyl ester and 9 ml of concentrated ammonia in 120 ml of n-propanol.
Yield: 59% of theory.

EXAMPLE 51

The compound of Example 49 was also obtained analogously to Example 3 by heating a solution of 500 mmols of 3'-nitrobenzylideneacetoacetic acid 4-chlorobenzyl ester and 50 mmols of β-aminocrotonic acid methyl ester in 90 ml of pyridine.
Yield: 65% of theory.

EXAMPLE 52

The compound of Example 49 was also obtained analogously to Example 4 by heating a solution of 50 mmols of 3'-nitrobenzylideneacetoacetic acid 4-chlorobenzyl ester, 50 mmols of acetoacetic acid methyl ester and 6 ml of concentrated ammonia in 90 ml of n-propanol.
Yield: 62% of theory.

EXAMPLE 53

The compound of Example 49 was also obtained analogously to Example 5 by heating a solution of 50 mmols of β-aminocrotonic acid 4-chlorobenzyl ester, 50 mmols of 3-nitrobenzaldehyde and 50 mmols of acetoacetic acid methyl ester in 90 ml of n-butanol.
Yield: 67% of theory.

EXAMPLE 54

The compound of Example 49 was also obtained analogously to Example 6 by heating a solution of 50 mmols of β-aminocrotonic acidmethyl ester, 50 mmols of 3-nitrobenzaldehyde and 50 mmols of acetoacetic acid 4-chlorobenzyl ester in 90 ml of ethanol.
Yield: 73% of theory.

EXAMPLES 55 to 60

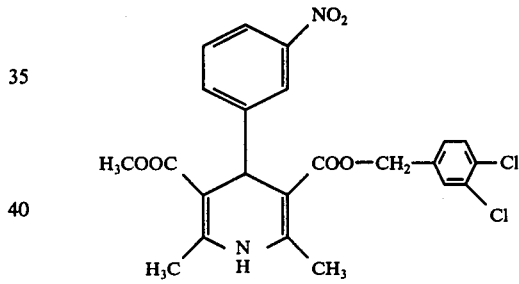

EXAMPLE 55

Analogously to Example 1 heating a solution of 75 mmols of 3'-nitrobenzylideneacetoacetic acid methyl ester and 75 mmols of β-aminocrotonic acid 3,4-dichlorobenzyl ester in 120 ml of ethanol gave 2,6-dimethyl-3-methoxycarbonyl-4-(3'-nitrophenyl)-1,4-dihydropyridine-5-carboxylic acid 3,4-dichlorobenzyl ester of melting point 149° C (from ethanol).
Yield: 75% of theory.

EXAMPLE 56

The compound of Example 55 was also obtained analogously to Example 2 by heating a solution of 75 mmols of 3'-nitrobenzylideneacetoacetic acid methyl ester, 75 mmols of acetoacetic acid 3,4-dichlorobenzyl ester and 9 ml of concentrated ammonia in 120 ml of n-butanol.
Yield: 62% of theory.

EXAMPLE 57

The compound of Example 55 was also obtained analogously to Example 3 by heating a solution of 50 mmols of 3'-nitrobenzylideneacetoacetic acid 3,4- dichlorobenzyl ester and 50 mmols of β-aminocrotonic acid methyl ester in 90 ml of n-propanol.
Yield: 67% of theory.

EXAMPLE 58

The compound of Example 55 was also obtained analogously to Example 4 by heating a solution of 50 mmols of 3'-nitrobenzylideneacetoacetic acid 3,4-dichlorobenzyl ester, 50 mmols of acetoacetic acid methyl ester and 6 ml of concentrated ammonia in 90 ml of methanol.
Yield: 60% of theory.

EXAMPLE 59

The compound of Example 55 was also obtained analogously to Example 5 by heating a solution of 50 mmols of β-aminocrotonic acid 3,4-dichlorobenzyl ester, 50 mmols of 3-nitrobenzaldehyde and 50 mmols of acetoacetic acid methyl ester in 90 ml of methanol.
Yield 59% of theory.

EXAMPLE 60

The compound of Example 55 was also obtained analogously to Example 6 by heating a solution of 50 mmols of β-aminocrotonic acid methyl ester, 50 mmols of 3-nitrobenzaldehyde and 50 mmols of acetoacetic acid 3,4-dichlorobenzyl ester in 90 ml of ethanol.
Yield: 62% of theory.

EXAMPLES 61 to 66

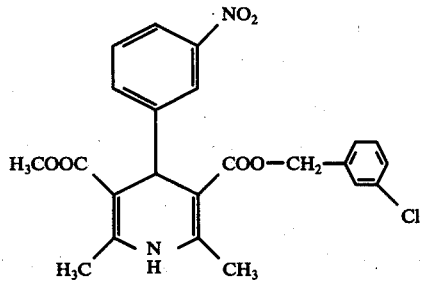

EXAMPLE 61

Analogously to Example 1 heating a solution of 75 mmols of 3'-nitrobenzylideneacetoacetic acid methyl ester and 75 mmols of β-aminocrotonic acid 3-chlorobenzyl ester in 120 ml of pyridine gave 2,6 dimethyl-3-methoxycarbonyl-4-(3'-nitrophenyl)-1,4-dihydropyridine-5-carboxylic acid 3-chlorobenzyl ester of melting point 142° C (from ethanol).
Yield: 70% of theory.

EXAMPLE 62

The compound of Example 61 was also obtained analogously to Example 2 by heating a solution of 75 mmols of 3'-nitrobenzylideneacetoacetic acid methyl ester, 75 mmols of acetoacetic acid 3-chlorobenzyl ester and 9 ml of concentrated ammonia in 120 ml of ethanol.
Yield: 63% of theory.

EXAMPLE 63

The compound of Example 61 was also obtained analogously to Example 3 by heating a solution of 50 mmols of 3'-nitrobenzylideneacetoacetic acid 3-chlorobenzyl ester and 50 mmols of β-aminocrotonic acid methyl ester in 90 ml of n-propanol.
Yield: 60% of theory.

EXAMPLE 64

The compound of Example 61 was also obtained analogously to Example 4 by heating a solution of 50 mmols of 3'-nitrobenzylideneacetoacetic acid 3-chlorobenzyl ester, 50 mmols of acetoacetic acid methyl ester of 6 ml of concentrated ammonia in 90 ml of methanol.
Yield: 55% of theory.

EXAMPLE 65

The compound of Example 61 was also obtained analogously to Example 5 by heating a solution of 50 mmols of β-aminocrotonic acid 3-chlorobenzyl ester, 50 mmols of 3-nitrobenzaldehyde and 50 mmols of acetoacetic acid methyl ester in 90 ml of methanol.
Yield: 56% of theory.

EXAMPLE 66

The compound of Example 61 was also obtained analogously to Example 6 by heating a solution of 50 mmols of β-aminocrotonic acid methyl ester, 50 mmols of 3-nitrobenzaldehyde and 50 mmols of acetoacetic acid 3-chlorobenzyl ester in 90 ml of ethanol.
Yield: 59% of theory.

EXAMPLES 67 to 72

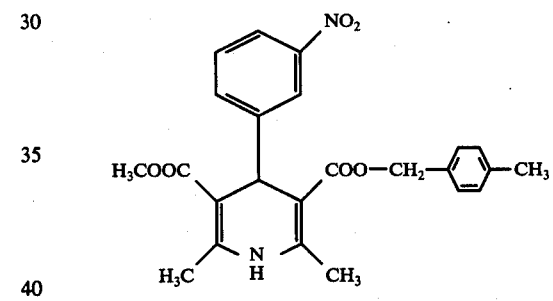

EXAMPLE 67

Analogously to Example 1 heating a solution of 75 mmols of 3'-nitrobenzylideneacetoacetic acid methyl ester and 75 mmols of β-aminocrotonic acid 4-methylbenzyl ester in 120 ml of ethanol gave 2,6-dimethyl-3-methoxycarbonyl-4-(3'-nitrophenyl)-1,4-dihydropyridine-5-carboxylic acid 4-methylbenzyl ester of melting point 112° C (from ethanol).
Yield: 65% of theory.

EXAMPLE 68

The compound of Example 67 was also obtained analogously to Example 2 by heating a solution of 75 mmols of 3'-nitrobenzlideneacetoacetic acid methyl ester, 75 mmols of acetoacetic acid 4-methylbenzyl ester and 9 ml of concentrated ammonia in 120 ml of ethanol.
Yield: 58% of theory.

EXAMPLE 69

The compound of Example 67 was also obtained analogously to Example 3 by heating a solution of 50 mmols of 3'-nitrobenzylideneacetoacetic acid 4-methylbenzyl ester and 50 mmols of β-aminocrotonic acid methyl ester in 90 ml of n-propanol.
Yield: 68% of theory.

EXAMPLE 70

The compound of Example 67 was also obtained analogously to Example 4 by heating a solution of 50 mmols of 3'-nitrobenzylideneacetoacetic acid 4-methyl-benzyl ester, 50 mmols of acetoacetic acid methyl ester and 6 ml of concentrated ammonia in 90 ml of methanol.
Yield: 60% of theory.

EXAMPLE 71

The compound of Example 67 was also obtained analogously to Example 5 by heating a solution of 50 mmols of β-aminocrotonic acid 4-methylbenzyl ester, 50 mmols of 3-nitrobenzaldehyde and 50 mmols of acetoacetic acid methyl ester in 90 ml of ethanol.
Yield: 65% of theory.

EXAMPLE 72

The compound of Example 67 was also obtained analogously to Example 6 by heating a solution of 50 mmols of β-aminocrotonic acid methyl ester, 50 mmols of 3-nitrobenzaldehyde and 50 mmols of acetoacetic acid 4-methylbenzyl ester in 90 ml of ethanol.
Yield: 61% of theory.

EXAMPLES 73 to 78

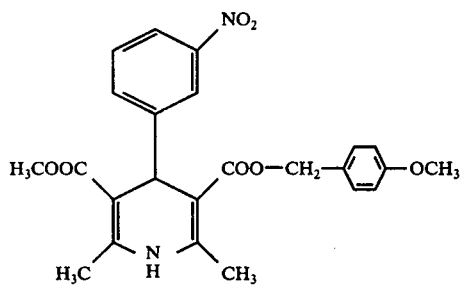

EXAMPLE 73

Analogously to Example 1 heating a solution of 75 mmols of 3'-nitrobenzylideneacetoacetic acid methyl ester and 75 mmols of β-aminocrotonic acid 4-methoxybenzyl ester in 120 ml of ethanol gave 2,6-dimethyl-3-methoxycarbonyl-4-(3'-nitrophenyl)-1,4-dihydropyridine-5-carboxylic acid 4-methoxybenzyl ester of melting point 136° C (from ethanol).
Yield: 75% of theory.

EXAMPLE 74

The compound of Example 73 was also obtained analogously to Example 2 by heating a solution of 75 mmols of 3'-nitrobenzylidieneacetoacetic acid methyl ester, 75 mmols of acetoacetic acid 4-methoxybenzyl ester and 9 ml of concentrated ammonia in 120 ml of ethanol.
Yield: 60% of theory.

EXAMPLE 75

The compound of Example 73 was also obtained analogously to Example 3 by heating a solution of 50 mmols of 3'-nitrobenzylideneacetoacetic acid 4-methoxybenzyl ester and 50 mmols of β-aminocrotonic acid methyl ester in 90 ml of ethanol.
Yield: 62% of theory.

EXAMPLE 76

The compound of Example 73 was also obtained analogously to Example 4 by heating a solution of 50 mmols of 3'-nitrobenzylideneacetoacetic acid 4-methoxybenzyl ester, 50 mmols of acetoacetic acid methyl ester and 6 ml of concentrated ammonia in 90 ml of methanol.
Yield: 59% of theory,

EXAMPLE 77

The compound of Example 73 was also obtained analogously to Example 5 by heating a solution of 50 mmols of β-aminocrotonic acid 4-methoxybenzyl ester, 50 mmols of 3-nitrobenzaldehyde and 50 mmols of acetoacetic acid methyl ester in 90 ml of ethanol.
Yield: 62% of theory.

EXAMPLE 78

The compound of Example 73 was also obtained analogously to Example 6 by heating a solution of 50 mmols of aminocrotonic acid methyl ester, 50 mmols of 3-nitrobenzaldehyde and 50 mmols of acetoacetic acid 4-methoxybenzyl ester in 90 ml of ethanol.
Yield: 58% of theory.

EXAMPLE 79 to 84

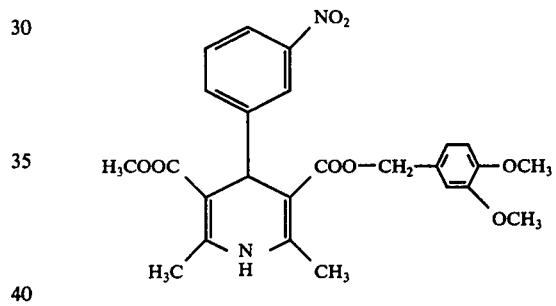

EXAMPLE 79

Analogously to Example 1 heating a solution of 75 mmols of 3'-nitrobenzylideneacetoacetic acid methyl ester and 75 mmols of β-aminocrotonic acid 3,4-dimethoxybenzyl ester in 120 ml of ethanol gave 2,6-dimethyl-3-methoxycarbonyl-4-(3'-nitrophenyl)-1,4-dihydropyridine-5-carboxylic acid 3,4-dimethoxybenzyl ester of melting point 129° C (from ethanol).
Yield: 75% of theory.

EXAMPLE 80

The compound of Example 79 was also obtained analogously to Example 2 by heating a solution of 75 mmols of 3'-nitrobenzylideneacetoacetic acid methyl ester, 75 mmols of acetoacetic acid 3,4-dimethoxybenzyl ester and 9 ml of concentrated ammonia in 120 mo of ethanol.
Yield: 62% of theory.

EXAMPLE 81

The compound of Example 79 was also obtained analogously to Example 3 by heating a solution of 50 mmols of 3'-nitrobenzylideneacetoacetic acid 3,4-dimethoxybenzyl ester and 50 mmols of β-aminocrotonic acid methyl ester in 90 ml of ethanol.
Yield: 68% of theory.

EXAMPLE 82

The compound of Example 79 was also obtained analogously to Example 4 by heating a solution of 50 mmols of 3'-nitrobenzylideneacetoacetic acid 3,4 -dimethoxybenzyl ester, 50 mmols of acetoacetic acid methyl ester and 6 ml of concentrated ammonia in 90 ml of methanol.

Yield: 59% of theory.

EXAMPLE 83

The compound of Example 79 was also obtained analogously to Example 5 by heating a solution of 50 mmols of β-aminocrotonic acid 3,4-dimethoxybenzyl ester, 50 mmols of 3-nitrobenzaldehyde and 50 mmols of acetoacetic acid methyl ester in 90 ml of ethanol.

Yield: 55% of theory.

Example 84

The compound of Example 79 was also obtained analogously to Example 6 by heating a solution of 50 mmols of β-amino crotonic acid methyl ester, 50 mmols of 3-nitrobenzaldehyde and 50 mmols of acetoacetic acid 3,4-dimethoxybenzyl ester in 90 ml of ethanol.

Yield: 57% of theory.

EXAMPLES 85 to 90

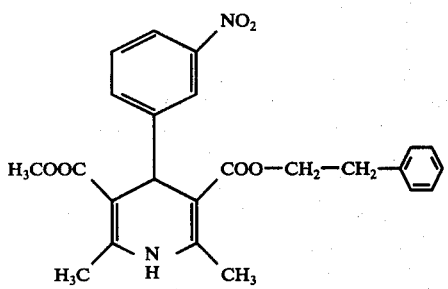

EXAMPLE 85

Analogously to Example 1 heating a solution of 75 mmols of 3'-nitrobenzylideneacetoacetic acid methyl ester and 75 mmols of β-aminocrotonic acid 2-phenylethyl ester in 120 ml of ethanol gave 2,6-dimethyl-3-methoxycarbonyl-4-(3'-nitrophenyl)-1,4-dihydropyridine-5-carboxylic acid 2-phenylethyl ester of melting point 122° C (from ethanol).

Yield: 74% of theory.

EXAMPLE 86

The compound of Example 85 was also obtained analogously to Example 2 by heating a solution of 75 mmols of 3'-nitrobenzylideneacetoacetic acid methyl ester, 75 mmols of acetoacetic acid 2-phenylethyl ester and 9 ml of concentrated ammonia in 120 ml of ethanol.

Yield: 61: of theory.

EXAMPLE 87

The compound of Example 85 was also obtained analogously to Example 3 by heating a solution of 50 mmols of 3'-nitrobenzylideneacetoacetic acid 2-phenylethyl ester and 50 mmols oc β-aminocrotonic acid methyl ester in 90 ml of ethanol.

Yield: 69% of theory.

EXAMPLE 88

The compound of Example 85 was also obtained analogously to Example 4 by heating a solution of 50 mmols of 3'-nitrobenzylideneacetoacetic acid 2-phenylethyl ester, 50 mmols of acetoacetic acid methyl ester and 6 ml of concentrated ammonia in 90 ml of methanol.

Yield: 59% of theory.

EXAMPLE 89

The compound of Example 85 was also obtained analogously to Example 5 by heating a solution of 50 mmols of β-aminocrotonic acid 2-phenylethyl ester, 50 mmols of 3-nitrobenzaldehyde and 50 mmols of acetoacetic acid methyl ester in 90 ml of ethanol.

Yield: 57% of theory.

EXAMPLE 90

The compound of Example 85 was also obtained analogously to Example 6 by heating a solution of 50 mmols of β-aminocrotonic acid methyl ester, 50 mmols of 3-nitrobenzaldehyde and 50 mmols of acetoacetic acid 2-phenylethyl ester in 90 ml of ethanol.

Yield: 55% of theory.

EXAMPLES 91 to 96

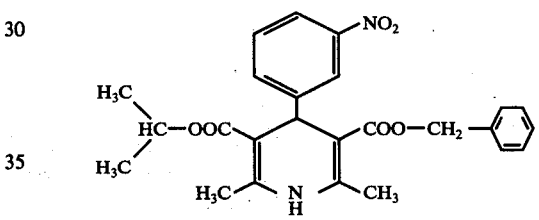

EXAMPLE 91

Analogously to Example 1 heating a solution of 75 mmols of 3'-nitrobenzylideneacetoacetic acid isoporpyl ester and 75 mmols of β-aminocrotonic acid benzyl ester in 120 ml of isopropanol gave 2,6-dimethyl-3-isopropoxycarbonyl-4-(3'-nitrophenyl)-1,4-dihydropyridine-5-carboxylic acid benzyl ester of melting point 121° C (from ethanol).

Yield: 71% of theory.

EXAMPLE 92

The compound of Example 91 as also obtained analogously to Example 2 by heating a solution of 75 mmols of 3'-nitrobenzylideneacetoacetic acid isopropyl ester, 75 mmols of acetoacetic acid benzyl ester and 9 ml of concentrated ammonia in 120 ml of ethanol.

Yield: 63% of theory.

EXAMPLE 93

The compound of Example 91 was also obtained analogously to Example 3 by heating a solution of 50 mmols of 3'-nitrobenzylideneacetoacetic acid benzyl ester and 50 mmols of β-aminocrotonic acid isoporpyl ester in 90 ml of isopropanol.

Yield: 75% of theory.

EXAMPLE 94

The compound of Example 91 was obtained analogously to example 4 by heating a solution of 50 mmol of 3'-nitrobenzylideneacetoacetic acid benzyl ester, 50 mmols of acetoacetic acid isopropyl ester and 6 ml of concentrated ammonia in 90 ml of ethanol.

Yield: 61% of theory.

EXAMPLE 95

The compound of Example 91 was also obtained analogously to Example 5 by heating a solution of 50 mmols of β-aminocrotonic acid benzyl ester, 50 mmols of 3-nitrobenzaldehyde and 50 mmols of acetoacetic acid isopropyl ester in 90 ml of isoproanol.

Yield: 58% of theory.

EXAMPLE 96

The compound of Example 91 was also obtained analogously to Example 6 by heating a solution of 50 mmols of β-aminocrotonic acid isopropyl ester, 50 mmols of 3-nitrobenzaldehyde and 50 mmols of acetoacetic acid benzyl ester in 90 ml of isopropanol.

Yield: 56% of theory.

EXAMPLES 97 to 102

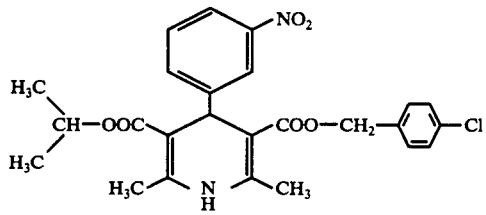

EXAMPLE 97

Analogously to Example 1 heating a solution of 75 mmols of 3'-nitrobenzylideneacetoacetic acid isopropyl ester and 75 mmols of β-aminocrotonic acid 4-chlorobenzyl ester in 120 ml of isopropanol gave 2,6-dimethyl-3-isopropoxycarbonyl-4-(3'-nitrophenyl)-1,4-dihydropyridine-5-carboxylic acid 4-chlorobenzyl ester of melting point 137° C (from ethanol).

Yield: 78% of theory.

EXAMPLE 98

The compound of Exaple 97 was also obtained analogously to Example 2 by heating a solution of 75 mmols of 3'-nitrobenzylideneacetoacetic acid isopropyl ester, 75 mmols of acetoacetic acid 4-chlorobenzyl ester and 9 ml of concentrated ammonia in 120 ml of ethanol.

Yield: 60% of theory.

EXAMPLE 99

The compound of Example 97 was also obtained analogously to Example 3 by heating a solution of 50 mmols of 3'-nitrobenzylideneacetoacetic acid 4-chlorobenzyl ester and 50 mmols of β-aminocrotonic acid isopropyl ester in 90 ml of isopropanol.

Yield: 74% of theory.

EXAMPLE 100

The compound of Example 97 was also obtaned analogously to Example 4 by heating a solution of 50 mmols of 3'-nitrobenzylideneacetonacetic acid 4-chlorobenzyl ester, 50 mmols of acetoacetic acid isopropyl ester and 6 ml of concentrated ammonia in 90 ml of ethanol.

Yield: 62% of theory.

EXAMPLE 101

The compound of Example 97 was also obtained analogously to Example 5 by heating a solution of 50 mmols of β-aminocrotonic acid 4-chlorobenzyl ester, 50 mmols of 3-nitrobenzaldehyde and 50 mmols of acetoacetic acid isopropyl ester in 90 ml of isopropanol.

Yield: 58% of theory.

EXAMPLE 102

The compound of Example 97 was also obtained analogously to Example 6 by heating a solution of 50 mmols of β-aminocrotonic acid isopropyl ester, 50 mmols of 3-nitrobenzaldehyde and 50 mmols of acetoacetic acid 4-chlorobenzyl ester in 90 ml of isopropanol.

Yield: 60% of theory.

EXAMPLE 103 to 108

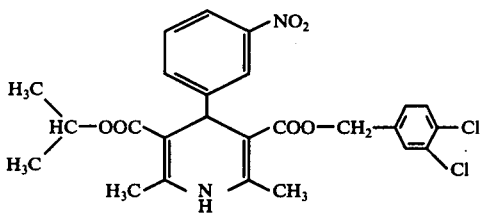

EXAMPLE 103

Analogously to Example 1 eating a solution of 75 mmols of 3'-nitrobenzylideneacetoacetic acid isopropyl ester and 75 mmols of β-aminocrotonic acid 3,4-dichlorobenzyl ester in 120 ml of isopropanol gave 2,6-dimethyl-3-isopropoxycarbonyl-4-(3'-nitrophenyl)-1,4-dihydropyridine-5-carboxylic acid 3, 4-dichlorobenzyl ester of melting point 155° C (from ethanol).

Yield: 75% of theory.

EXAMPLE 104

The compound of Example 103 was also obtained analogously to Example 2by heating a solution of 75 mmols of 3'-nitrobenzylideneacetoacetic acid isopropyl ester, 75 mmols of acetoacetic acid 3,4-dichlorobenzyl ester and 9 ml of concentrated ammonia in 120 ml of ethanol.

Yield: 62% of theory.

EXAMPLE 105

The compound of Example 103 was also obtained analogously to Example 3 by heating a solution of 50 mmols of 3'-nitrobenzlideneacetoacetic acid 3,4-dichlorobenzyl ester and 50 mmols of β-aminocrotonic acid isopropyl ester in 90 ml of isopropanol.

Yield: 70% of theory.

EXAMPLE 106

The compound of Example 103 was also obtained analogously to Example 4 by heating a solution of 50 mmols of 3'-nitrobenzylideneacetoacetic acid 3,4-dichlorobenzyl ester, 50 mmols of acetoacetic acid isopropyl ester and 6 ml of concentrated ammonia in 90 ml of ethanol.

Yield: 59% of theory.

EXAMPLE 107

The compound of Example 103 was also obtained analogously to Example 5 by heating a solution of 50 mmols of β-aminocrotonic acid 3,4-dichlorobenzyl ester, 50 mmols of 3-nitrobenzaldehyde and 50 mmols of acetoacetic acid isopropyl ester in 90 ml of isopropanol.

Yield: 55% of theory.

EXAMPLE 108

The compound of Example 103 was also obtained analogously to Example 6 by heating a solution of 50 mmols of β-aminocrotonic acid isopropyl ester, 50 mmols of 30-nitrobenzaldehyde and 50 mmols of acetoacetic acid 3,4-dichlorobenzyl ester in 90 ml of isopropanol.

Yield: 58% of theory.

EXAMPLES 109 to 114

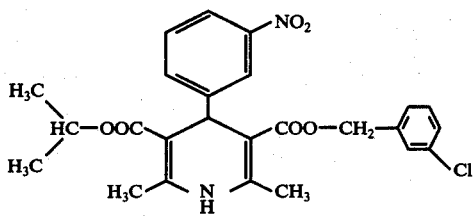

EXAMPLE 109

Analogously to Example 1 heating a solution of 75 mmols of 3'-nitrobenzylideneacetoaceic acid isopropyl ester and 75 mmols of β-aminocrotonic acid 3-chlorobenzyl ester in 120 ml of isopropanol gave 2,6-dimethyl-3-isopropoxycarbonyl-4-(3'-nitrophenyl)-1,4-dihydropyridine-5-carboxylic acid 3-chlorobenzyl ester of melting point 104° C (from ethanol).

Yield: 69% of theory.

EXAMPLE 110

The compound of Example 109 was also obtained analogously to Example 2 by heating a solution of 75 mmols of 3'-nitrobenzlideneacetoacetic acid isopropyl ester, 75 mmols of acetoacetic acid 3-chlorobenzyl ester and 9 ml of concentrated ammonia in 120 of ethanol.

Yield: 56% of theory.

EXAMPLE 111

The compound of Example 109 was also obtained analogously to Example 3 by heating a solution of 50 mmols of 3'-nitrobenzylideneacetoacetic acid 3-chlorobenzyl ester and 50 mmols of β-aminocrotonic acid isopropyl ester in 90 ml of isopropanol.

Yield: 65% of theory.

EXAMPLE 112

The compound of Example 109 was also obtained analogously to Example 4 by heating a solution of 50 mmols of 3'-nitrobenzylideneacetoacetic acid 3-chlorobenzyl ester, 50 mmols of acetoacetic acid isopropyl ester and 6 ml of concentrated ammonia in 90 ml of ethanol.

Yield: 57% of theory.

EXAMPLE 113

The compound of Example 109 was also obtained analogously to Example 5 by heating a solution of 50 mmols of β-amino crotonic acid 3-chlorobenzyl ester, 50 mmols of 3-nitrobenzaldehyde and 50 mmols of acetoacetic acid isopropyl ester in 90 ml of isopropanol.

Yield: 60% of theory.

EXAMPLE 114

The compound of Example 109 was also obtained analogously to Example 6 by heating a solution of 50 mmols of β-aminocrotonic acid isopropyl ester, 50 mmols of 3-nitrobenzaldehyde and 50 mmols of acetoacetic acid 3-chlorobenzyl ester in 90 ml of isopropanol.

Yield: 57% of theory.

EXAMPLES 115 to 120

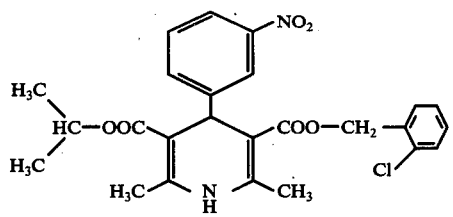

EXAMPLE 115

Analogously to Example 1 heating a solution of 75 mmols of 3'-nitrobenzylideneacetoacetic acid isopropyl ester and 75 mmols of β-aminocrotonic acid 2-chlorobenzyl ester in 120 ml of ethanol gave 2,6-dimethyl-3-isopropoxycarbonyl-4-(3'-nitrophenyl)-1,4-dihydropyridine-5-carboxylic acid 2-chlorobenzyl ester of melting point 103° C (from ethanol).

Yield: 73% of theory.

EXAMPLE 116

The compound of Example 115 was also obtained analogously to Example 2 by heating a solution of 75 mmols of 3'-nitrobenzylideneacetoacetic acid isopropyl ester, 75 mmols of acetoacetic acid 2-chlorobenzyl ester and 9 ml of concentrated ammonia in 120 ml of ethanol.

Yield: 61% of theory.

EXAMPLE 117

The compound of Example 115 was also obtained analogously to Example 3 by heating a solution of 50 mmols of 3'-nitrobenzylideneacetoacetic acid 2-chlorobenzyl ester and 50 mmols of β-aminocrotonic acid isopropyl ester in 90 ml of ethanol.

Yield: 68% of theory.

EXAMPLE 118

The compound of Example 115 was also obtained analogously to Example 4 by heating a solution of 50 mmols of 3'-nitrobenzylideneacetoacetic acid 2-chlorobenzyl ester, 50 mmols of acetoacetic acid isopropyl ester of 6 ml of concentrated ammonia in 90 ml of ethanol.

Yield: 55% of theory.

EXAMPLE 119

The compound of Example 115 was also obtained analogously to Example 5 by heating a solution of 50 mmols of β-aminocrotonic acid 2-chlorobenzyl ester, 50 mmols of 3-nitrobenzaldehyde and 50 mmols of acetoacetic acid isopropyl ester in 90 ml of isopropanol.

Yield: 58% of theory.

EXAMPLE 120

The compound of Example 115 was also obtained analogously to Example 6 by heating a solution of 50 mmols of β-amino-crotonic acid isopropyl ester, 50 mmols of 3-nitrobenzaldehyde and 50 mmols of acetoacetic acid 2-chlorobenzyl ester in 90 ml of isopropanol.

Yield 54% of theory.

EXAMPLES 121 to 126

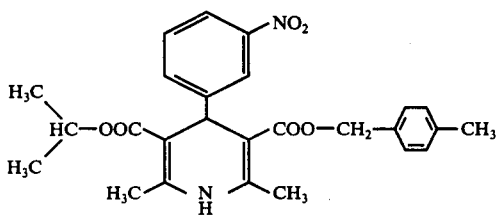

EXAMPLE 121

Analogously to Example 1 heating a solution of 75 mmols of 3'-nitrobenzylideneacetoacetic acid isopropyl ester and 75 mmols of β-aminocrotonic acid 4-methylbenzyl ester in 120 ml of ethanol gave 2,6-dimethyl-3-isopropoxycarbonyl-4-(3'-nitrophenyl)1,4-dihydropyridine-5-carboxylic acid 4-methylbenzyl ester of melting point 106° C (from ethanol).

Yield: 75% of theory.

EXAMPLE 122

The compound of Example 121 was also obtained analogously to Example 2 by heating a solution of 75 mmols of 3'-nitrobenzylideneacetoacetic acid isopropyl ester, 75 mmols of acetoacetic acid 4-methylbenzyl ester and 9 ml of concentrated ammonia in 120 ml of ethanol.

Yield: 63% of theory.

EXAMPLE 123

The compound of Example 121 was also obtained analogously to Example 3 by heating a solution of 50 mmols of 3'-nitrobenzylideneacetoacetic acid 4-methylbenzyl ester and 50 mmols of β-aminocrotonic acid isopropyl ester in 90 ml of ethanol.

Yield 71% of theory.

EXAMPLE 124

The compound of Example 121 was also obtained analogously to Example 4 by heating a solution of 50 mmols 3'-nitrobenzylideneacetoacetic acid 4-methylbenzyl ester, 50 mmols of acetoacetic acid isopropyl ester and 6 ml of concentrated ammonia in 90 ml of ethanol.

Yield: 59% of theory.

EXAMPLE 125

The compound of Example 121 was also obtained analogously to Example 5 by heating a solution of 50 mmols of β-aminocrotonic acid 4-methylbenzyl ester, 50 mmols of 3-nitrobenzaldehyde and 50 mmols of acetoacetic acid isopropyl ester in 90 ml of isopropanol.

Yield: 61% of theory.

EXAMPLE 126

The compound of Example 121 was also obtained analogously to Example 6 by heating a solution of 50 mmols of β-amino crotonic acid isopropyl ester, 50 mmols of 3-nitrobenzaldehyde and 50 mmols of acetoacetic acid 4-methylbenzyl ester in 90 ml of isopropanol.

Yield: 56% of theory.

EXAMPLES 127 to 132

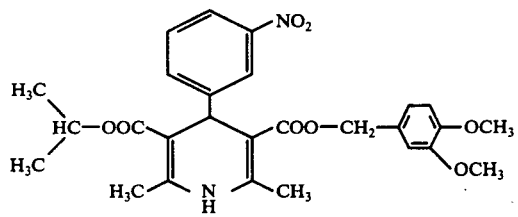

EXAMPLE 127

Analogously to Example 1 heating a solution of 75 mmols of 3'-nitrobenzylideneacetoacetic acid isopropyl ester and 75 mmols of β-aminocrotonic acid 3,4-dimethoxybenzyl ester in 120 ml of isopropanol gave 2,6-dimethyl-3-isopropoxycarbonyl-4-(3'-nitrophenyl)-1,4-dihydropyridine-5-carboxylic acid 3,4-dimethoxybenzyl ester of melting point 154° C (from ethanol).

Yield: 77% of theory.

EXAMPLE 128

The compound of Example 127 was also obtained analogously to Example 2 by heating a solution of 75 mmols of 3'-nitrobenzylideneacetoacetic acid isopropyl ester, 75 mmols of acetoacetic acid 3,4-dimethoxybenzyl ester and 9 ml of concentrated ammonia in 120 ml of ethanol.

Yield: 61% of theory.

EXAMPLE 129

The compound of Example 127 was also obtained analogously to Example 3 by heating a solution of 50 mmols of 3'-nitrobenzylideneacetoacetic acid 3,4-dimethoxybenzyl ester and 50 mmols of β-aminocrotonic acid isopropyl ester in 90 ml of ethanol.

Yield: 75% of theory.

EXAMPLE 130

The compound of Example 127 was also obtained analogously to Example 4 by heating a solution of 50 mmols of 3'-nitrobenzylideneacetoacetic acid 3,4-dimethoxybenzyl ester, 50 mmols of acetoacetic acid isopropyl ester and 6 ml of concentrated ammonia in 90 ml of ethanol.

Yield: 62% of theory.

EXAMPLE 131

The compound of Example 127 was also obtained analogously to Example 5 by heating a solution of 50 mmols of β-aminocrontonic acid 3,4-dimethoxybenzyl ester, 50 mmols of 3-nitrobenzaldehyde and 50 mmols of acetoacetic acid isopropyl ester in 90 ml of isopropanol.

Yield: 59% of theory.

EXAMPLE 132

The compound of Example 127 was also obtained analogously to Example 6 by heating a solution of 50 mmols of β-aminocrotonic acid isopropyl ester, 50 mmols of 3-nitrobenzaldehyde and 50 mmols of acetoacetic acid 3,4-dimethoxybenzyl ester in 90 ml of ethanol. Yield: 55% of theory.

EXAMPLES 133 to 138

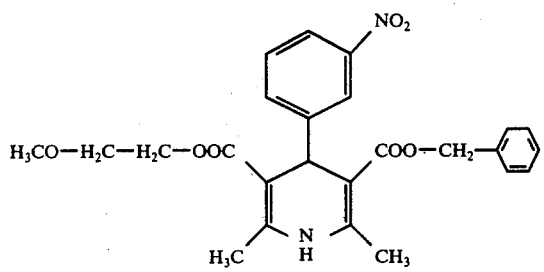

EXAMPLE 133

Analogously to Example 1 heating a solution of 75 mmols of 3'-nitrobenzylideneacetoacetic acid 2-methoxyethyl ester and 75 mmols of β-aminocrotonic acid benzyl ester in 120 ml of ethanol gave 2,6-dimethyl-3-(2-methoxyethyloxy)-carbonyl-4-(3'-nitrophenyl)-1,4-dihydropyridine-5-carboxylic acid benzyl ester of melting point 152° C (from ethanol).
Yield: 79% of theory.

EXAMPLE 134

The compound of Example 133 was also obtained analogously to Example 2 by heating a solution of 75 mmols of 3'-nitrobenzylideneacetoacetic acid 2-methoxyethyl ester, 75 mmols of acetoacetic acid benzyl ester and 9 ml of concentrated ammonia in 120 ml of ethanol.
Yield: 68% of theory.

EXAMPLE 135

The compound of Example 133 was also obtained analogously to Example 3 by heating a solution of 50 mmols of 3'-nitrobenzylideneacetoacetic acid benzyl ester and 50 mmols of β-aminocrotonic acid 2-methoxyethyl ester in 90 ml of ethanol.
Yield: 72% of theory.

EXAMPLE 136

The compound of Exalime 133 was also obtained analogously to Example 4 by heating a solution of 50 mmols of 3'-nitrobenzylideneacetoacetic acid benzyl ester, 50 mmols of acetoacetic acid 2-methoxyethyl ester and 6 ml of concentrated ammonia in 90 ml of ethanol.
Yield: 64% of theory.

EXAMPLE 137

The compound of Example 133 was also obtained analogously to Example 5 by heating a solution of 50 mmols of β-aminocrotonic acid benzyl ester, 50 mmols of 3-nitrobenzaldehyde and 50 mmols of acetoacetic acid 2-methoxyethyl ester in 90 ml of ethanol.
Yield: 64% of theory.

EXAMPLE 138

The compound of Example 133 was also obtained analogously to Example 6 by heating a solution of 50 mmols of β-aminocrotonic acid 2-methoxyethyl ester, 50 mmols of 3-nitrobenzaldehyde and 50 mmols of acetoacetic acid benzyl ester in 90 ml of ethanol.
Yield: 57% of theory.

EXAMPLE 139 to 144

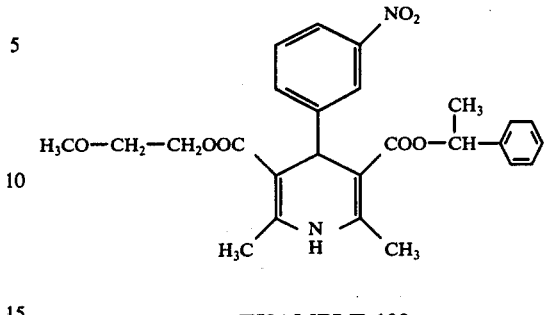

EXAMPLE 139

Analogously to Example 1 heating a solution of 75 mmols of 3'-nitrobenzylideneacetoacetic acid 2-methoxyethyl ester and 75 mmols of β-aminocrotonic acid 1-phenylethyl ester in 120 ml of ethanol gave 2,6-dimethyl-3-(2-methoxyethyloxy)-carbonyl-4-(3'-nitroethyl) 5 carboxylic acid 1-phenyl ethyl ester of melting point 122° C (from ethanol).
Yield: 68% of theory.

EXAMPLE 140

The compound of Example 139 was also obtained analogously to Example 2 by heating a solution of 75 mmols of 3'-nitrobenzylideneacetoacetic acid 2-methoxyethyl ester, 75 mmols of acetoacetic acid 1-phenylethyl ester and 9 ml of concentrated ammonia in 120 ml of ethanol.
Yield: 59% of theory.

EXAMPLE 141

The compound of Example 139 was also obtained analogously to Example 3 by heating a solution of 50 mmols of 3'-nitrobenzylideneacetoacetic acid 1-phenylethyl ester and 50 mmols of β-aminocrotonic acid 2-methoxyethyl ester in 90 ml of ethanol.
Yield: 61% of theory.

EXAMPLE 142

The compound of Example 139 was also obtained analogously to Example 4 by heating a solution of 50 mmols of 3'-nitrobenzylideneacetoacetic acid 1-phenylethyl ester, 50 mmols of acetoacetic acid 2-methoxyethyl ester and 6 ml of concentrated ammonia in 90 ml of ethanol.
Yield: 54% of theory.

EXAMPLE 143

The compound of Example 139 was also obtained analogously to Example 5 by heating a solution of 50 mmols of β-aminocrotonic acid 1-phenylethyl ester, 50 mmols of 3-nitrobenzaldehyde and 50 mmols of acetoacetic acid 2-methoxyethyl ester in 90 ml of ethanol.
Yield: 57% of theory.

EXAMPLE 144

The compound of Example 139 was also obtained analogously to Example 6 by heating a solution of 50 mmols of β-aminocrotonic acid 2-methoxyethyl ester, 50 mmols of 3-nitrobenzaldehyde and 50 mmols of acetoacetic acid 1-phenylethyl ester in 90 ml of ethanol.
Yield: 52% of theory.

EXAMPLES 145 to 150

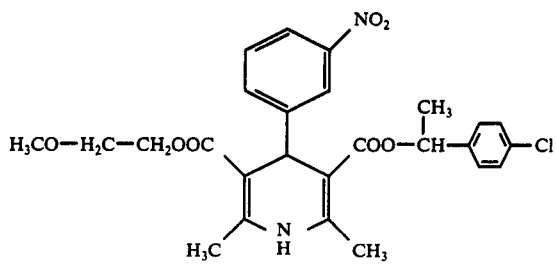

EXAMPLE 145

Analogously to Example 1 heating a solution of 75 mmols of 3'-nitrobenzylideneacetoacetic acid 2-methoxyethyl ester and 75 mmols of β-aminocrotonic acid 1-(4-chlorophenyl)-ethyl ester in 120 ml of ethanol gave 2,6-dimethyl-3-(2-methoxyethyloxy)-carbonyl-4-(3'-nitrophenyl)-1,4-dihydropyridine-5-carboxylic acid 1-(4-chlorophenyl)-ethyl ester of melting point 106° C (from ethanol).

Yield: 72% of theory.

EXAMPLE 146

The compound of Example 145 was also obtained analogously to Example 2 by heating a solution of 75 mmols of 3'-nitrobenzylideneacetoacetic acid 2-methoxyethyl ester, 75 mmols of acetoacetic acid (1-(4-chlorophenyl)-ethyl ester and 9 ml of concentrated ammonia in 120 ml of ethanol.

Yield: 60% of theory.

EXAMPLE 147

The compound of Example 145 was also obtained analogously to Example 3 by heating a solution of 50 mmols of 3'-nitrobenzylideneacetoacetic acid 1-(4-chlorophenyl)-ethyl ester and 50 mmols of β-aminocrotonic acid 2-methoxyethyl ester in 90 ml of ethanol.

Yield: 66% of theory.

EXAMPLE 148

The compound of Example 145 was also obtained analogously to Example 4 by heating a solution of 50 mmols of 3'-nitrobenzylideneacetoacetic acid 1-(4-chlorophenyl)-ethyl ester, 50 mmols of acetoacetic acid 2-methoxyethyl ester and 6 ml of concentrated ammonia in 90 ml of ethanol.

Yield: 58% of theory.

EXAMPLE 149

The compound of Example 145 was also obtained analogously to Example 5 by heating a solution of 50 mmols of β-aminocrotonicacid 1-(4-chlorophenyl)-ethyl ester, 50 mmols of 3-nitrobenzaldehyde and 50 mmols of acetoacetic acid 2-methoxyethyl ester in 90 ml of ethanol.

Yield: 59% of theory.

EXAMPLE 150

The compound of Example 145 was also obtained analogously to Example 6 by heating a solution of 50 mmols of β-aminocrotonic acid 2-methoxyethyl ester, 50 mmols of 3-nitrobenzaldehyde and 50 mmols of acetoacetic acid 1-(4-chlorophenyl)-ethyl ester in 90 ml of ethanol.

Yield: 54% of theory.

EXAMPLES 151 to 156

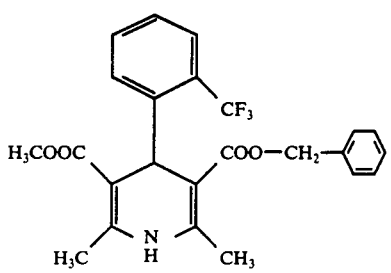

EXAMPLE 151

Analogously to Example 1 heating a solution of 75 mmols of 2'-trifluoromethylbenzylideneacetoacetic acid methyl ester and 75 mmols of β-aminocrotonic acid benzyl ester in 120 ml of ethanol gave 2,6-dimethyl-3-methoxycarbonyl-4-'2'-trifluoromethylphenyl)-1,4-dihydropyridine-5-carboxylic acid benzyl ester of melting point 136° C (from ethanol).

Yield: 75% of theory.

EXAMPLE 152

The compound of Example 151 was also obtained analogously to Example 2 by heating a solution of 75 mmols of 2'-trifluoromethylbenzylideneacetoacetic acid methyl ester, 75 mmols of acetoacetic acid benzyl ester and 9 ml of concentrated ammonia in 120 ml of ethanol.

Yield: 66% of theory.

EXAMPLE 153

The compound of Example 151 was also obtained analogously to Example 3 by heating a solution of 50 mmols of 2'-trifluoromethylbenzylideneacetoacetic acid benzyl ester and 50 mmols of β-aminocrotonic acid methyl ester in 90 ml of ethanol.

Yield: 71% of theory.

EXAMPLE 154

The compound of Example 151 was also obtained analogously to Example 4 by heating a solution of 50 mmols of 2'-trifluoromethylbenzylideneacetoacetic acid benzyl ester, 50 mmols of acetoacetic acid methyl ester and 6 ml of concentrated ammonia in 90 ml of ethanol.

Yield: 60% of theory.

EXAMPLE 155

The compound of Example 151 was also obtained analogously to Example 5 by heating a solution of 50 mmols of β-aminocrotonic acid benzyl ester, 50 mmols of 2-trifluoromethylbenzaldehyde and 50 mmols of acetoacetic acid methyl ester in 90 ml of ethanol.

Yield: 52% of theory.

EXAMPLE 156

The compound of Example 151 was also obtained analogously to Example 6 by heating a solution of 50 mmols of β-aminocrotonic acid methyl ester, 50 mmols of 2-trifluoromethylbenzaldehyde and 50 mmols of acetoacetic acid benzyl ester in 90 ml of ethanol.

Yield: 54% of theory.

EXAMPLES 157 to 162

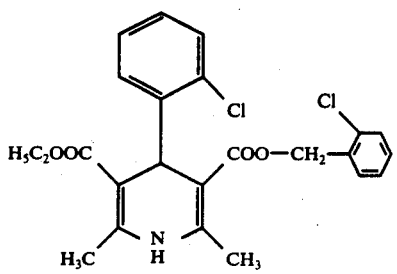

EXAMPLE 157

Analogously to Example 1 heating a solution of 75 mmols of 2'-chlorobenzylideneacetoacetic acid ethyl ester and 75 mmols of β-aminocrotonic acid 2-chlorobenzyl ester in 120 ml of ethanol gave 2,6-dimethyl-3-ethoxycarbonyl-4-(2'-chlorophenyl)-1,4-dihydropyridine-5-carboxylic acid 2-chlorobenzyl ester of melting point 120° C (from ethanol).

Yield: 63% of theory.

EXAMPLE 158

The compound of Example 157 was also obtained analogously to Example 2 by heating a solution of 75 mmols of 2'-chlorobenzylideneacetoacetic acid ethyl ester, 75 mmols of acetoacetic acid 2-chlorobenzyl ester and 9 ml of concentrated ammonia in 120 ml of methanol.

Yield: 54% of theory.

EXAMPLE 159

The compound of Example 157 was also obtained analogously to Example 3 by heating a solution of 50 mmols of 2'-chlorobenzylideneacetoacetic acid 2-chlorobenzyl ester and 50 mmols of β-aminocrotonic acid ethyl ester in 90 ml of ethanol.

Yield: 59% of theory.

EXAMPLE 160

The compound of Example 157 was also obtained analogously to Example 4 by heating a solution of 50 mmols of 2'-chlorobenzylideneacetoacetic acid 2-chlorobenzyl ester, 50 mmols of acetoacetic acid ethyl ester and 6 ml of concentrated ammonia in 90 ml of ethanol.

Yield: 52% of theory.

EXAMPLE 161

The compound of Example 157 was also obtained analogously to Example 5 by heating a solution of 50 mmols of β-aminocrotonic acid 2-chlorobenzyl ester, 50 mmols of 2-chlorobenzaldehyde and 50 mmols of acetoacetic acid ethyl ester in 90 ml of ethanol.

Yield: 53% of theory.

EXAMPLE 162

The compound of Example 157 was also obtained analogously to Example 6 by heating a solution of 50 mmols of β-aminocrotonic acid ethyl ester, 50 mmols of 2-chlorobenzaldehyde and 50 mmols of acetoacetic acid 2-chlorobenzyl ester in 90 ml of ethanol.

Yield: 50% of theory.

EXAMPLES 163 to 168

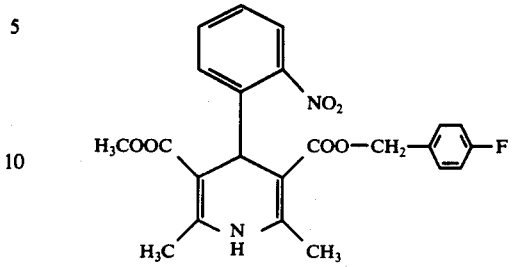

EXAMPLE 163

Analogously to Example 1 heating a solution of 75 mmols of 2'-nitrobenzylideneacetoacetic acid methyl ester and 75 mmols of β-aminocrotonic acid 4-fluorobenzyl ester in 120 ml of ethanol gave 2,6-dimethyl-3-methoxycarbonyl-4-(2'-nitrophenyl)-1,4-dihydropyridine-5-carboxylic acid 4-fluorobenyzl ester of melting point 117° C (from ethanol).

Yield: 75% of theory.

EXAMPLE 164

The compound of Example 163 was also obtained analogously to Example 2 by heating a solution of 75 mmols of 2'-nitrobenzylideneacetoacetic acid methyl ester, 75 mmols of acetoacetic acid 4-fluorobenzyl ester and 9 ml of concentrated ammonia in 120 ml of ethanol.

Yield: 63% of theory.

EXAMPLE 165

The compound of Example 163 was also obtained analogously to Example 3 by heating a solution of 50 mmols of 2'-nitrobenzylideneacetoacetic acid 4-fluorobenzyl ester, and 50 mmols of β-aminocrotonic acid methyl ester in 90 ml of methanol.

Yield: 71% of theory.

EXAMPLE 166

The compound of Example 163 was also obtained analogously to Example 4 by heating a solution of 50 mmols of 2'-nitrobenzylideneacetoacetic acid 4-fluorobenzyl ester, 50 mmols of acetoacetic acid methyl ester and 6ml of concentrated ammonia in 90 ml of ethanol.

Yield: 62% of theory.

EXAMPLE 167

The compound of Example 163 was also obtained anaogously to Example 5 by heating a solution of 50 mmols of β-aminocrotonic acid 4-fluorobenzyl ester, 50 mmols of 2-nitrobenzaldehyde and 50 mmols of acetoacetic acid methyl ester in 90 ml of ethanol.

Yield: 56% of theory.

EXAMPLE 168

The compound of Example 163 was also obtained analogously to Example 6 by heating a solution of 50 mmols of β-aminocrotonic acid methyl ester, 50 mmols of 2-nitrobenzaldehyde and 50 mmols of acetoacetic acid 4-fluorobenzyl ester in 90 ml of ethanol.

Yield: 52% of theory.

EXAMPLES 169 to 174

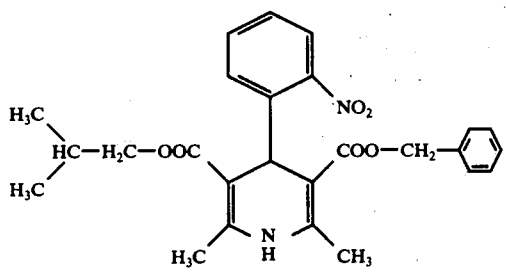

EXAMPLE 169

Analogously to Example 1 heating a solution of 75 mmols of 2'-nitrobenzylideneacetoacetic acid isobutyl ester and 75 mmols of β-aminocrotonic acid benzyl ester in 120 ml of ethanol gave 2,6-dimethyl-3-isobutoxycarbonyl-4-(2'-nitrophenyl)-1,4-dihydropyridine-5-carboxylic acid benzyl ester of melting point 154° C (from ethanol).

Yield: 71% of theory.

EXAMPLE 170

The compound of Example 169 was also obtained analogously to Example 2 by heating a solution of 75 mmols of 2'-nitrobenzylideneacetoacetic acid isobutyl ester, 75 mmols of acetoacetic acid benzyl ester and 9 ml of concentrated ammonia in 120 ml of ethanol.

Yield: 59% of theory.

EXAMPLE 171

The compound of Example 169 was also obtained analogously to Example 3 by heating a solution of 50 mmols of 2'-nitrobenzylideneacetoacetic acid benzyl ester and 50 mmols of β-aminocrotonic acid isobutyl ester in 90 ml of ethanol.

Yield: 73% of theory.

EXAMPLE 172

The compound of Example 169 was also obtained analogously to Example 4 by heating a solution of 50 mmols of 2'-nitrobenzylideneacetoacetic acid benzyl ester, 50 mmols of acetoacetic acid isobutyl ester and 6 ml of concentrated ammonia in 90 ml of ethanol.

Yield: 62% of theory.

EXAMPLE 173

The compound of Example 169 was also obtained analogously to Example 5 by heating a solution of 50 mmols of β-aminocrotonic acid benzyl ester, 50 mmols of 2-nitrobenzaldehyde and 50 mmols of acetoacetic acid isobutyl ester in 90 ml of ethanol.

Yield: 59% of theory.

EXAMPLE 174

The compound of Example 169 was also obtained analogously to Example 5 by heating a solution of 50 mmols of β-aminocrotonic acid isobutyl ester, 50 mmols of 2-nitrobenzaldehyde and 50 mmols of acetoacetic acid benzyl ester in 90 ml of ethanol.

Yield: 56% of theory.

EXAMPLES 175 to 180

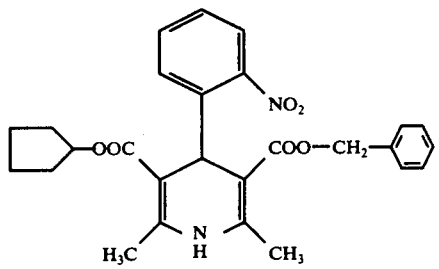

EXAMPLE 175

Analogously to Example 1 heating a solution of 75 mmols of 2'-nitrobenzylideneacetoacetic acid cyclopentyl ester and 75 mmols of β-aminocrotonic acid benzyl ester in 120 ml of ethanol gave 2,6-dimethyl-3-cyclopentyloxycarbonyl-4-(2'-nitrophenyl)-1,4-dihydropyridine-5-carboxylic acid benzyl ester of melting point 111° C (from ethanol).

Yield: 73% of theory.

EXAMPLE 176

The compound of Example 175 was also obtained analogously to Example 2 by heating a solution of 75 mmols of 2'-nitrobenzylideneacetoacetic acid cyclopentyl ester, 75 mmols of acetoacetic acid benzyl ester and 9 ml of concentrated ammonia in 120 ml of ethanol.

Yield: 61% of theory.

EXAMPLE 177

The compound of Example 175 was also obtained analogously to Example 3 by heating a solution of 50 mmols of 2'-nitrobenzylideneacetoacetic acid benzyl ester and 50 mmols of β-aminocrotonic acid cyclopentyl ester in 90 ml of ethanol.

Yield: 68% of theory.

EXAMPLE 178

The compound of Example 175 was also obtained analogously to Example 4 by heating a solution of 50 mmols of 2'-nitrobenzylideneacetoacetic acid benzyl ester, 50 mmols of acetoacetic acid cyclopentyl ester and 6 ml of concentrated ammonia in 90 ml of ethanol.

Yield: 57% of theory.

EXAMPLE 179

The compound of Example 175 was also obtained analogously to Example 5 by heating a solution of 50 mmols of β-aminocrotonic acid benzyl ester, 50 mmols of 2-nitrobenzaldehye and 50 mmols of acetoacetic acid cyclopentyl ester in 90 ml of ethanol.

Yield: 55% of theory.

EXAMPLE 180

The compound of Example 175 was also obtained analogously to Example 6 by heating a solution of 50 mmols of β-aminocrotonic acid cyclopentyl ester, 50 mmols of 2-nitrobenzaldehyde and 50 mmols of acetoacetic acid benzyl ester in 90 ml of ethanol.

Yield: 52% of theory.

EXAMPLE 181 to 186

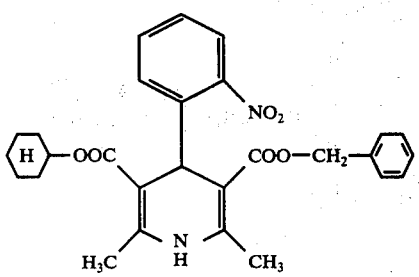

EXAMPLE 181

Analogously to Example 1 heating a solution of 75 mmols of 2'-nitrobenzylideneacetoacetic acid cyclohexyl ester and 75 mmols of β-aminocrotonic acid benzyl ester in 120 ml of ethanol gave 2,6-dimethyl-3-cyclohexyloxycarbonyl-4-(2'-nitrophenyl)-1,4-dihydropyridine-5-carboxylic acid benzyl ester of melting point 134° C (from ethanol).

Yield: 68% of theory.

EXAMPLE 182

The compound of Example 181 was also obtained analogously to Example 2 by heating a solution of 75 mmols of 2'-nitrobenzylideneacetoacetic acid cyclohexyl ester, 75 mmols of acetoacetic acid benzyl ester and 9 ml of concentrated ammonia in 120 ml of ethanol.

Yield: 59% of theory.

EXAMPLE 183

The compound of Example 181 was also obtained analogously to Example 3 by heating a solution of 50 mmols of 2'-nitrobenzylideneacetoacetic acid benzyl ester and 50 mmols of β-aminocrotonic acid cyclohexyl ester in 90 ml of ethanol.

Yield: 63% of theory.

EXAMPLE 184

The compound of Example 181 was also obtained analogously to Example 4 by heating a solution of 50 mmols of 2'-nitrobenzylideneacetoacetic acid benzyl ester, 50 mmols of acetoacetic acid cyclohexyl ester and 6 ml of concentrated ammonia in 90 ml of ethanol.

Yield: 58% of theory.

EXAMPLE 185

The compound of Example 181 was also obtained analogously to Example 5 by heating a solution of 50 mmols of β-aminocrotonic acid benzyl ester, 50 mmols of 2-nitrobenzaldehyde and 50 mmols of acetoacetic acid cyclohexyl ester in 90 ml of ethanol.

Yield: 57% of theory.

EXAMPLE 186

The compound of Example 181 was also obtained analogously to Example 6 by heating a solution of 50 mmols of β-aminocrotonic acid cyclohexyl ester, 50 mmols of 2-nitrobenzaldehyde and 50 mmols of acetoacetic acid benzyl ester in 90 ml of ethanol.

Yield: 52% of theory.

EXAMPLES 187 to 192

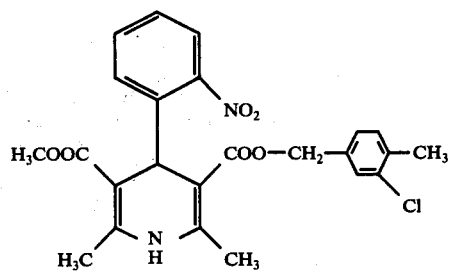

EXAMPLE 187

Analogously to Example 1 heating a solution of 75 mmols of 2'-nitrobenzylideneacetoacetic acid methyl ester and 75 mmols of β-aminocrotonic acid 3-chloro-4-methylbenzyl ester in 120 ml of ethanol gave 2,6-dimethyl-3-methoxycarbonyl-4-(2'-nitrophenyl)-1,4-dihydropyridine-5-carboxylic acid 3-chloro-4-methylbenzyl ester of melting point 132° C (from ethanol).

Yield: 72% of theory.

EXAMPLE 188

The compound of Example 187 was also obtained analogously to Example 2 by heating a solution of 75 mmols of 2'-nitrobenzylideneacetoacetic acid methyl ester, 75 mmols of acetoacetic acid 3-chloro- 4-methylbenzyl ester and 9 ml of concentrated ammonia in 120 ml of ethanol.

Yield: 61% of theory.

EXAMPLE 189

The compound of Example 187 was also obtained analogously to Example 3 by heating a solution of 50 mmols of 2'-nitrobenzylideneacetoacetic acid 3-chloro-4-methylbenzyl ester and 50 mmols of β-aminocrotonic acid methyl ester in 90 ml of ethanol.

Yield: 62% of theory.

EXAMPLE 190

The compound of Example 187 was also obtained analogously to Example 4 by heating a solution of 50 mmols of 2'-nitrobenzylideneacetoacetic acid 3-chloro-4-methylbenzyl ester, 50 mmols of acetoacetic acid methyl ester and 6 ml of concentrated ammonia in 90 ml of ethanol.

Yield: 53% of theory.

EXAMPLE 191

The compound of Example 187 was also obtained analogously to Example 5 by heating a solution of 50 mmols of β-aminocrotonic acid 3-chloro-4-methylbenzyl ester, 50 mmols of 2-nitrobenzaldehyde and 50 mmols of acetoacetic acid methyl ester in 90 ml of ethanol.

Yield: 51% of theory.

EXAMPLE 192

The compound of Example 187 was also obtained analogously to Example 6 by heating a solution of 50 mmols of β-aminocrotonic acid methyl ester, 50 mmols of 2-nitro-benzaldehyde and 50 mmols of acetoacetic acid 3-chloro- 4-methylbenzyl ester in 90 ml of ethanol.

Yield: 54% of theory.

EXAMPLES 193 to 198

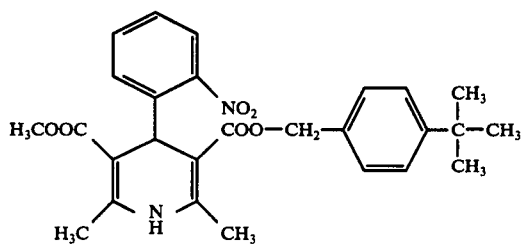

EXAMPLE 193

Analogously to Example 1 heating a solution of 75 mmols of 2'-nitrobenzylideneacetoacetic acid methyl ester and 75 mmols of β-aminocrotonic acid 4-tert.-butylbenzyl ester in 120 ml of ethanol gave 2,6-dimethyl-3-methoxycarbonyl-4-(2'-nitrophenyl)-1,4-dihydropyridine-5-carboxylic acid 4-tert.-butylbenzyl ester of melting point 146° C (from ethanol).
Yield: 75% of theory.

EXAMPLE 194

The compound of Example 193 was also obtained analogously to Example 2 by heating a solution of 75 mmols of 2'-nitrobenzylideneacetoacetic acid methyl ester, 75 mmols of acetic acid 4-tert.-butyl benzyl ester and 9 ml of concentrated ammonia in 120 ml of ethanol.
Yield: 60% of theory.

EXAMPLE 195

The compound of Example 193 was also obtained analogously to Example 3 by heating a solution of 50 mmols of 2'-nitrobenzylideneacetoacetic acid 4-tert.-butylbenzyl ester and 50 mmols of β-aminocrotonic acid methyl ester in 90 ml of ethanol.
Yield: 64% of theory.

EXAMPLE 196

The compound of Example 194 was also obtained analogously to Example 4 by heating a solution of 50 mmols of 2'-nitrobenzylideneacetoacetic acid 4 -tert.-butylbenzyl ester, 50 mmols of acetoacetic acid methyl ester and 6 ml of concentrated ammonia in 90 ml of ethanol.
Yield: 55% of theory.

EXAMPLE 197

The compound of Example 193 was also obtained analogously to Example 5 by heating a solution of 50 mmols of β-aminocrotonic acid 4-tert.-butylbenzyl ester, 50 mmols of 2-nitrobenzaldehyde and 50 mmols of acetoacetic acid methyl ester in 90 ml of ethanol.
Yield: 51% of theory.

EXAMPLE 198

The compound of Example 193 was also obtained analogously to Example 6 by heating a soluton of 50 mmols of β-aminocrotonic acid methyl ester, 50 mmols of 2-nitrobenzaldehyde and 50 mols of acetoacetic acid 4-tert.-butylbenzyl ester in 90 ml of ethanol.
Yield: 54% of theory.

EXAMPLES 199 TO 204

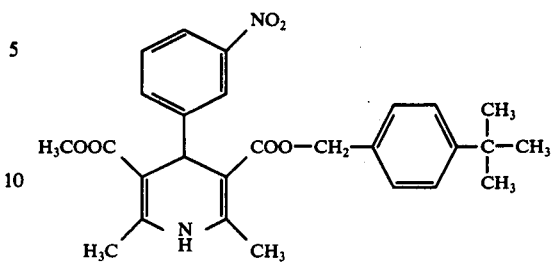

EXAMPLE 199

Analogously to Example 1 heating a solution of 75 mmols of 3'-nitrobenzylideneacetoacetic acid methyl ester and 75 mmols of β-aminocrotonic acid 4-tert.-butylbenzyl ester in 120 ml of ethanol gave 2,6-dimethyl-3-methoxycarbonyl-4-(3'-nitrophenyl)-1,4-dihydropyridine-5-carboxylic acid 4-tert.-butylbenzyl ester of melting point 161° C (from ethanol).
Yield: 78% of theory.

EXAMPLE 200

The compound of Example 199 was also obtained analogously to Example 12 by heating a solution of 75 mmols of 3'-nitrobenzylideneacetoacetic acid methyl ester, 75 mmols of acetoacetic acid 4-tert.-butylbenzyl ester and 9 ml of concentrated ammonia in 120 ml of ethanol.
Yield: 65% of theory.

EXAMPLE 201

The compound of Example 199 was also obtained analogously to Example 3 by heating a solution of 50 mmols of 3'-nitrobenzylideneacetoacetic acid 4-tert.-butylbenzyl ester and 50 mmols of β-aminocrotonic acid methyl ester in 90 ml of ethanol.
Yield: 67% of theory.

EXAMPLE 202

The compound of Example 199 was also obtained analogously to Example 4 by heating a solution of 50 mmols of 3'-nitrobenzylideneacetoacetic acid 4-tert.-butylbenzyl ester, 50 mmols of acetoacetic acid methyl ester and 7 ml of concentrated ammonia in 90 ml of ethanol.
Yield: 59% of theory.

EXAMPLE 203

The compound of Example 199 was also obtained analogously to Example 5 by heating a solution of 50 mmols of β-aminocrotonic acid 4-tert.-butylbenzyl ester, 50 mmols of 3-nitrobenzaldehyde and 50 mmols of acetoacetic acid methyl ester in 90 ml of ethanol.
Yield: 55% of theory.

EXAMPLE 204

The compound of Example 199 was also obtained analogously to Example 6 by heating a solution of 50 mmols of β-aminocrotonic acid methyl ester, 50 mmols of 3-nitrobenzaldehyde and 50 mmols of acetoacetic acid 4-tert.-butylbenzyl ester in 90 ml of ethanol.
Yield: 51% of theory.

EXAMPLES 205 TO 210

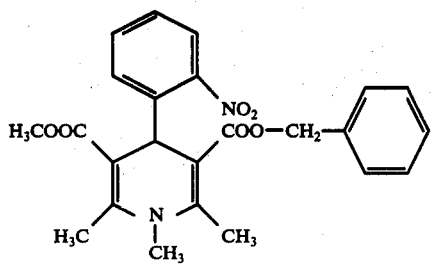

EXAMPLE 205

Analogously to Example 1 heating a solution of 75 mmols of 2'-nitrobenzylideneacetoacetic acid methyl ester and 75 mmols of β-methylaminocrotonic acid benzyl ester in 120 ml of ethanol gave 1,2,6-trimethyl-3-methoxycarbonyl-4-(2'-nitrophenyl)-1,4-dihydropyridine-5-carboxylic acid benzyl ester of melting point 182° C (from ethanol/dimethylformamide).

Yield: 67% of theory.

EXAMPLE 206

The compound of Example 205 was also obtained analogously to Example 2 by heating a solution of 75 mmols of 2'-nitrobenzylideneacetoacetic acid methyl ester, 75 mmols of acetoacetic acid benzyl ester and 9 ml of a 30% strength aqueous methylamine solution in 120 ml of ethanol.

Yield: 52% of theory.

EXAMPLE 207

The compound of Example 205 was also obtained analogously to Example 3 by heating a solution of 50 mmols of 2'-nitrobenzylideneacetoacetic acid benzyl ester and 50 mmols of β-methylaminocrotonic acid methyl ester in 90 ml of ethanol.

Yield: 61% of theory.

EXAMPLE 208

The compound of Example 205 was also obtained analogously to Example 4 by heating a solution of 50 mmols of 2'-nitrobenzylideneacetoacetic acid benzyl ester, 50 mmols of acetoacetic acid methyl ester and 6 ml of a 30% strength methylamine solution in 90 ml of ethanol.

Yield: 50% of theory.

EXAMPLE 209

The compound of Example 205 was also obtained analogously to Example 5 by heating a solution of 50 mmols of β-methylaminocrotonic acid benzyl ester, 50 mmols of 2-nitrobenzaldehyde and 50 mmols of acetoacetic acid methyl ester in 90 ml of ethanol.

Yield: 52% of theory.

EXAMPLE 210

The compound of Example 205 was also obtained analogously to Example 6 by heating a solution of 50 mmols of 2-nitrobenzaldehyde and 50 mmols of acetoacetic acid benzyl ester in 90 ml of ethanol.

Yield: 49% of theory.

EXAMPLE 211 TO 216

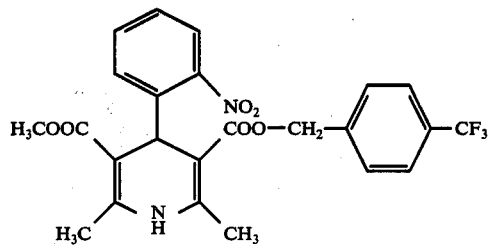

EXAMPLE 211

Analogously to Example 1 heating a solution of 75 mmols of 2'-nitrobenzylideneacetoacetic acid methyl ester and 75 mmols of β-aminocrotonic acid 4-trifluoromethylbenzyl ester in 120 ml of ethanol gave 2,6-dimethyl-3-methoxycarbonyl-4-(2'-nitrophenyl)-1,4-dihydropyridine-5-carboxylic acid 4-trifluoromethylbenzyl ester of melting point 130° C (from ethanol).

Yield: 72% of theory.

EXAMPLE 212

The compound of Example 211 was also obtained analogously to Example 2 by heating a solution of 75 mmols of 2'-nitrobenzylideneacetoacetic acid methyl ester, 75 mmols of acetoacetic acid 4-trifluoromethylbenzyl ester and 9 ml of concentrated ammonia in 120 ml of ethanol.

Yield: 61% of theory.

EXAMPLE 213

The compound of Example 211 was also obtained analogously to Example 3 by heating a solution of 50 mmols of 2'-nitrobenzylideneacetoacetic acid 4-trifluoromethylbenzyl ester and 50 mmols of β-aminocrotonic acid methyl ester in 90 ml of ethanol.

Yield: 63% of theory.

EXAMPLE 214

The compound of Example 211 was also obtained analogously to Example 4 by heating a solution of 50 mmols of 2'-nitrobenzylideneacetoacetic acid 4-trifluoromethylbenzyl ester, 50 mmols of acetoacetic acid methyl ester and 6 ml of concentrated ammonia in 90 ml of ethanol.

Yield: 52% of theory.

EXAMPLE 215

The compound of Example 211 was also obtained analogously to Example 5 by heating a solution of 50 mmols of β-aminocrotonic acid 4-trifluoromethylbenzyl ester, 50 mmols of 2-nitrobenzaldehyde and 50 mmols of acetoacetic acid methyl ester in 90 ml of ethanol.

Yield: 54% of theory.

EXAMPLE 216

The compound of Example 211 was also obtained analogously to Example 6 by heating a solution of 50 mmols of β-aminocrotonic acid methyl ester, 50 mmols of 2-nitrobenzaldehyde and 50 mmols of acetoacetic acid 4-trifluoromethylbenzyl ester in 90 ml of ethanol.

Yield: 50% of theory.

EXAMPLE 217 TO 222

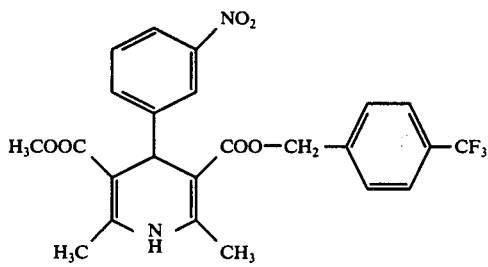

EXAMPLE 217

Analogously to Example 1 heating a solution of 75 mmols of 3'-nitrobenzylideneacetoacetic acid methyl ester and 75 mmols of β-aminocrotonic acid 4-trifluoromethylbenzyl ester in 120 ml of ethanol gave 2,6-dimethyl-3-methoxycarbonyl-4-(3'-nitrophenyl)-1,4-dihydropyridine-5-carboxylic acid 4-trifluoromethylbenzyl ester of melting point 163° C (from ethanol).
Yield: 75% of theory.

EXAMPLE 218

The compound of Example 217 was also obtained nalogously to Example 2 by heating a solution of 75 mmols of 3'-nitrobenzylideneacetoacetic acid methyl ester, 75 mmols of acetoacetic acid 4-trifluoromethylbenzyl ester and 9 ml of concentrated ammonia in 120 ml of ethanol.
Yield: 63% of theory.

EXAMPLE 219

The compound of Example 217 was also obtained analogously to Example 3 by heating a solution of 50 mmols of 3'-nitrobenzylideneacetoacetic acid 4-trifluoromethylbenzyl ester and 50 mmol of β-aminocrotonic acid methyl ester in 90 ml of ethanol. Yield: 64% of theory.

EXAMPLE 220

The compound of Example 217 was also obtained analogously to Example 4 by heating a solution of 50 mmols of 3'-nitrobenzylideneacetoacetic acid 4-trifluoromethylbenzyl ester, 50 mmols of acetoacetic acid methyl ester and 6 ml of concentrated ammonia in 90 ml of ethanol.
Yield: 55% of theory.

EXAMPLE 221

The compound of Example 217 was also obtained analogously to Example 5 by heating a solution of 50 mmols of β-aminocrotonic acid 4-trifluoromethylbenzyl ester, 50 mmols of 3-nitrobenzaldehyde and 50 mmols of acetoacetic acid methyl ester in 90 ml of ethanol.
Yield: 51% of theory.

EXAMPLE 222

The compound of Example 217 was also obtained analogously to Example 6 by heating a solution of 50 mmols of β-aminocrotonic acid methyl ester, 50 mmols of 3-nitrobenzaldehyde and 50 mmols of acetoacetic acid 4-trifluoromethylbenzyl ester in 90 ml of ethanol.
Yield: 48% of theory.

EXAMPLES 223 TO 228

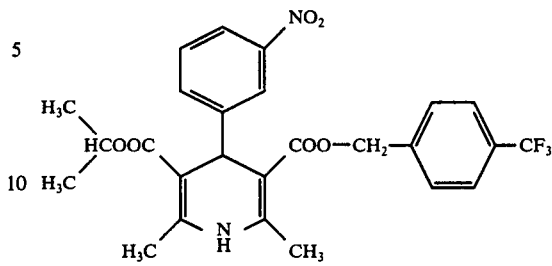

EXAMPLE 223

Analogously to Example 1 heating a solution of 75 mmols of 3'-nitrobenzylideneacetoacetic acid isopropyl ester and 75 mmols of β-aminocrotonic acid 4-trifluoromethylbenzyl ester in 120 ml of ethanol gave 2,6-dimethyl-3-isopropoxycarbonyl-4-(3'-nitrophenyl)-1,4-dihydropyridine-5-carboxylic acid 4-trifluoromethylbenzyl ester of melting point 139° C (from ethanol).
Yield: 76% of theory.

EXAMPLE 224

The compound of Example 223 was also obtained analogously to Example 2 by heating a solution of 75 mmols of 3'-nitrobenzylideneacetoacetic acid isopropyl ester, 75 mmols of acetoacetic acid 4-trifluoromethylbenzyl ester and 9 ml of concentrated ammonia in 120 ml of ethanol.
Yield: 62% of theory.

EXAMPLE 225

The compound of Example 223 was also obtained analogously to Example 3 by heating a solution of 50 mmols of 3'-nitrobenzylideneacetoacetic acid 4-trifluoromethylbenzyl ester and 50 mmols of β-aminocrotonic acid isopropyl ester in 90 ml of ethanol.
Yield: 68% of theory.

EXAMPLE 226

The compound of Example 223 was also obtained analogously to Example 4 by heating a solution of 50 mmols of 3'-nitrobenzylideneacetoacetic acid 4-trifluoromethylbenzyl ester, 50 mmols of acetoacetic acid isopropyl ester and 6 ml of concentrated ammonia in 90 ml of ethanol.
Yield: 53% of theory.

EXAMPLE 227

The compound of Example 223 was also obtained analogously to Example 5 by heating a solution of 50 mmols of β-aminocrotonic acid 4-trifluoromethylbenzyl ester, 50 mmols of 3-nitrobenzaldehyde and 50 mmols of acetoacetic acid isopropyl ester in 90 ml of ethanol.
Yield: 51% of theory.

EXAMPLE 228

The compound of Example 223 was also obtained analogously to Example 6 by heating a solution of 50 mmols of β-aminocrotonic acid isopropyl ester, 50 mmols of 3-nitrobenzaldehyde and 5 mmols of acetoacetic acid 4-trifluoromethylbenzyl ester in 90 ml of ethanol.
Yield: 47% of theory.

EXAMPLES 229 TO 234

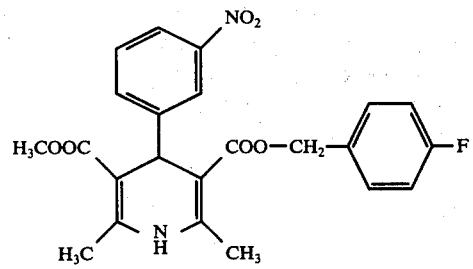

EXAMPLE 229

Analogously to Example 1 heating a solution of 75 mmols of 3'-nitrobenzylideneacetoacetic acid methyl ester and 75 mmols of β-aminocrotonic acid 4-fluorobenzyl ester in 120 ml of ethanol gave 2,6-dimethyl-3-methoxycarbonyl-4-(3'-nitrophenyl)-1,4-dihydropyridine-5-carboxylic acid 4-fluorobenzyl ester of melting point 168° C (from ethanol).

Yield: 74% of theory.

EXAMPLE 230

The compound of Example 229 was also obtained analogously to Example 2 by heating a solution of 75 mmols of 3'-nitrobenzylideneacetoacetic acid methyl ester, 75 mmols of acetoacetic acid 4-fluorobenzyl ester and 9 ml of concentrated ammonia in 120 ml of ethanol.

Yield: 65% of theory.

EXAMPLE 231

The compound of Example 229 was also obtained analogously to Example 3 by heating a solution of 50 mmols of 3'-nitrobenzylideneacetoacetic acid 4-fluorobenzyl ester and 50 mmols of β-aminocrotonic acid methyl ester in 90 ml of ethanol.

Yield: 70% of theory.

EXAMPLE 232

The compound of Example 229 was also obtained analogously to Example 4 by heating a solution of 50 mmols of 3'-nitrobenzylideneacetoacetic acid 4-fluorobenzyl ester, 50 mmols of acetoacetic acid methyl ester and 6 ml of concentrated ammonia in 90 ml of ethanol.

Yield: 59% of theory.

EXAMPLE 233

The compound of Example 229 was also obtained analogously to Example 5 by heating a solution of 50 mmols of β-aminocrotonic acid 4-fluorobenzyl ester, 50 mmols of 3-nitrobenzaldehyde and 50 mmols of acetoacetic acid methyl ester in 90 ml of ethanol.

Yield: 54% of theory.

Example 234

The compound of Example 229 was also obtained analogously to Example 6 by heating a solution of 50 mmols of β-aminocrotonic acid methyl ester, 50 mmols of 3-nitrobenzaldehyde and 50 mmols of acetoacetic acid 4-fluorobenzyl ester in 90 ml of ethanol.

Yield: 50% of theory.

EXAMPLE 235 TO 240

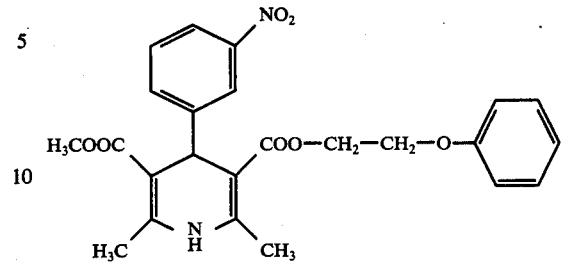

EXAMPLE 235

Analogously to Example 1 heating a solution of 75 mmols of 3'-nitrobenzylideneacetoacetic acid methyl ester and 75 mmols of β-aminocrotonic acid 2-phenoxyethyl ester in 120 ml of ethanol gave 2,6-dimethyl-3-methoxycarbonyl-4-(3'-nitrophenyl)-5-carboxylic acid 2-phenoxyalkyl ester of melting point 13° C (from ethanol).

Yield: 70% of theory.

EXAMPLE 236

The compound of Example 235 was also obtained analogously to Example 2 by heating a solution of 75 mmols of 3'-nitrobenzylideneacetoacetic acid methyl ester, 75 mmols of acetoacetic acid 2-phenoxyethyl ester and 9 ml of concentrated ammonia in 120 ml of ethanol.

Yield: 58% of theory.

EXAMPLE 237

The compound of Example 235 was also obtained analogously to Example 3 by heating a solution of 50 mmols of 3'-nitrobenzylideneacetoacetic acid 2-phenoxyethyl ester and 50 mmols of β-aminocrotonic acid methyl ester in 90 ml of ethanol. Yield: 61% of theory.

EXAMPLE 238

The compound of Example 235 was also obtained analogously to Example 4 by heating a solution of 50 mmols of 3'-nitrobenzylideneacetoacetic acid 2-phenoxyethyl ester, 50 mmols of acetoacetic acid methyl ester and 6 ml of concentrated ammonia in 90 ml of ethanol.

Yield: 54% of theory.

EXAMPLE 239

The compound of Example 235 was also obtained analogously to Example 5 by heating a solution of 50 mmols of β-aminocrotonic acid 2-phenoxyethyl ester, 50 mmols of 3-nitrobenzaldehyde and 50 mmols of acetoacetic acid methyl ester in 90 ml of ethanol.

Yield: 50% of theory.

EXAMPLE 240

The compound of Example 235 was also obtained analogously to Example 6 by heating a solution of 50 mmols of β-aminocrotonic acid methyl ester, 50 mmols of 3-nitrobenzaldehyde and 50 mmols of acetoacetic acid 2-phenoxyethyl ester in 90 ml of ethanol.

Yield: 45% of theory.

EXAMPLES 241 to 246

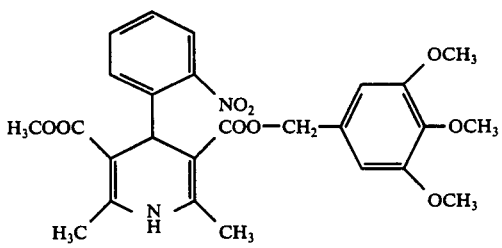

EXAMPLE 241

Analogously to Example 1 heating a solution of 75 mmols of 2'-nitrobenzylideneacetoacetic acid methyl ester and 75 ml of β-aminocrotonic acid 3,4,5-trimethoxybenzyl ester in 120 ml of ethanol gave 2,6-dimethyl-3-methoxycarbonyl-4-(2'-nitrophenyl)-1,4-dihydropyridine-5-carboxylic acid 3,4,5-trimethoxybenzyl ester of melting point 125° C (from ethanol).
Yield: 78% of theory.

EXAMPLE 242

The compound of Example 241 was also obtained analogously to Example 2 by heating a solution of 75 mmols of 2'-nitrobenzylideneacetoacetic acid methyl ester, 75 mmols of acetoacetic acid 3,4,5-trimethoxybenzyl ester and 9 ml of concentrated ammonia in 120 ml of ethanol.
Yield: 65% of theory.

EXAMPLE 243

The compound of Example 241 was also obtained analogously to Example 3 by heating a solution of 50 mmols of 2'-nitrobenzylideneacetoacetic acid 3,4,5-trimethoxybenzyl ester and 50 mmols of β-aminocrotonic acid methyl ester in 90 ml of ethanol.
Yield: 69% of theory.

EXAMPLE 244

The compound of Example 241 was also obtained analogously to Example 4 by heating a solution of 50 mmols of 2'-nitrobenzylideneacetoacetic acid 3,4,5-trimethoxybenzyl ester, 50 mmols of acetoacetic acid methyl ester and 6 ml of concentrated ammonia in 90 ml of ethanol.
Yield: 55% of theory.

EXAMPLE 245

The compound of Example 241 was also obtained analogously to Example 5 by heating a solution of 50 mmols of β-aminocrotonic acid 3,4,5-trimethoxybenzyl ester, 50 mmols of 2-nitrobenzaldehyde and 50 mmols of acetoacetic acid methyl ester in 90 ml of ethanol.
Yield: 52% of theory.

EXAMPLE 246

The compound of Example 241 was also obtained analogously to Example 6 by heating a solution of 50 mmols of β-aminocrotonic acid methyl ester, 50 mmols of 2-nitrobenzaldehyde and 50 mmols of acetoacetic acid 3,4,5-trimethoxybenzyl ester in 90 ml of ethanol.
Yield: 49% of theory.

EXAMPLES 247 TO 252

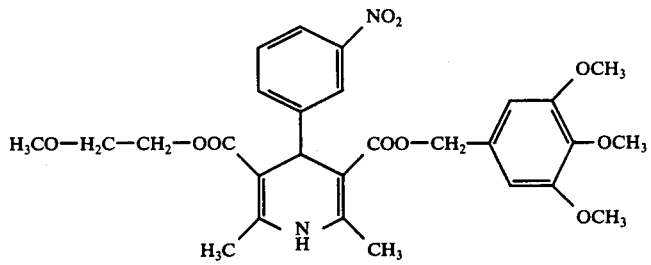

EXAMPLE 247

Analogously to Example 1 heating a solution of 75 mmols of 3'-nitrobenzylideneacetoacetic acid 2-methoxyethyl ester and 75 mmols of β-aminocrotonic acid 3,4,5-trimethoxybenzyl ester in 120 ml of ethanol gave 2,6-dimethyl-3-(2-methoxyethoxy)-carbonyl-4-(3'-nitrophenyl)-1,4-dihydropyridine-5-carboxylic acid 3,4,5-trimethoxybenzyl ester of melting point 160° C (from ethanol).
Yield: 71% of theory.

EXAMPLE 248

The compound of Example 247 was also obtained analogously to Example 2 by heating a solution of 75 mmols of 3'-nitrobenzylideneacetoacetic acid 2-methoxyethyl ester, 75 mmols of acetoacetic acid 3,4,5-trimethoxybenzyl ester and 9 ml of concentrated ammonia in 120 ml of ethanol.
Yield: 60% of theory.

EXAMPLE 249

The compound of Example 247 was also obtained analogously to Example 3 by heating a solution of 50 mmols of 3'-nitrobenzylideneacetoacetic acid 3,4,5-trimethoxybenzyl ester and 50 mmols of β-aminocrotonic acid 2-methoxyethyl ester in 90 ml of ethanol.
Yield: 66% of theory.

EXAMPLE 250

The compound of Example 247 was also obtained analogously to Example 4 by heating a solution of 50 mmols of 3'-nitrobenzylideneacetoacetic acid 3,4,5-trimethoxybenzyl ester, 50 mmols of acetoacetic acid 2-methoxyethyl ester and 6 ml of concentrated ammonia in 90 ml of ethanol.
Yield: 57% of theory.

EXAMPLE 251

The compound of Example 247 was also obtained analogously to Example 5 by heating a solution of 50 mmols of β-aminocrotonic acid 3,4,5-trimethoxybenzyl ester, 50 mmols of 3-nitrobenzaldehyde and 50 mmols of acetoacetic acid 2-methoxyethyl ester in 90 ml of ethanol.

Yield: 53% of theory.

EXAMPLE 252

The compound of Example 247 was also obtained analogously to Example 6 by heating a solution of 50 mmols of β-aminocrotonic acid 2-methoxyethyl ester, 50 mmols of 3-nitrobenzaldehyde and 50 mmols of acetoacetic acid 3,4,5-trimethoxybenzyl ester in 90 ml of ethanol.

Yield: 49% of theory.

EXAMPLES 253 TO 258

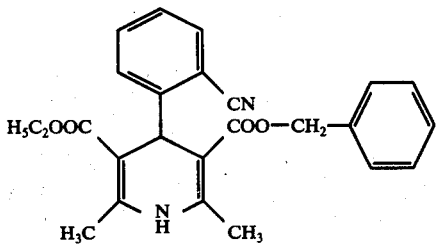

EXAMPLE 253

Analogously to Example 1 heating a solution of 75 mmols of 2'-cyanobenzylideneacetoacetic acid ethyl ester and 75 mmols of β-aminocrotonic acid benzyl ester in 120 ml of ethanol gave 2,6-dimethyl-3-ethoxycarbonyl-4-(2'-cyanophenyl)-1,4-dihydropyridine-5-carboxylic acid benzyl ester of melting point 136° C (from ethanol).

Yield: 65% of theory.

EXAMPLE 254

The compound of Example 253 was also obtained analogously to Example 2 by heating a solution of 75 mmols of 2'-cyanobenzlideneacetoacetic acid ethyl ester, 75 mmols of acetoacetic acid benzyl ester and 9 ml of concentrated ammonia in 120 ml of ethanol.

Yield: 54% of theory.

EXAMPLE 255

The compound of Example 253 was also obtained analogously to Example 3 by heating a solution of 50 mmols of 2'-cyanobenzylideneacetoacetic acid benzyl ester and 50 mmols of β-aminocrotonic acid ethyl ester in 90 ml of ethanol.

Yield: 59% of theory.

EXAMPLE 256

The compound of Example 253 was also obtained analogously to Example 4 by heating a solution of 50 mmols of 2'-cyanobenzylideneacetoacetic acid benzyl ester, 50 mmols of acetoacetic acid ethyl ester and 6 ml of concentrated ammonia in 90 ml of ethanol.

Yield: 49% of theory.

EXAMPLE 257

The compound of Example 253 was also obtained analogously to Example 5 by heating a solution of 50 mmols of β-aminocrotonic acid benzyl ester, 50 mmols of 2-cyanobenzaldehyde and 50 mmols of acetoacetic acid ethyl ester in 90 ml of ethanol.

Yield: 45% of theory.

EXAMPLE 258

The compound of Example 253 was also obtained analogously to Example 6 by heating a solution of 50 mmols of β-aminocrotonic acid ethyl ester, 50 mmols of 2-cyanobenzaldehyde and 50 mmols of acetoacetic acid benzyl ester and 90 ml of ethanol.

Yield: 42% of theory.

EXAMPLES 259 TO 264

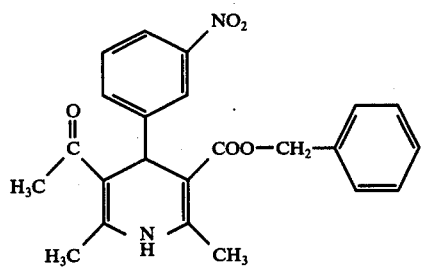

EXAMPLE 259

Analogously to Example 1 heating a solution of 75 mmols of 3'-nitrobenzylideneacetylacetone and 75 mmols of β-aminocrotonic acid benzyl ester in 120 ml of ethanol gave 2,6-dimethyl-3-acetyl-4-(3'-nitrophenyl)-1,4-dihydropyridine-5-carboxylic acid benzyl ester of melting point 152° C (from ethanol).

Yield: 67% of theory.

EXAMPLE 260

The compound of Example 259 was also obtained analogously to Example 2 by heating a solution of 75 mmols of 3'-nitrobenzylideneacetylacetone, 75 mmols of acetoacetic acid benzyl ester and 9 ml of concentrated ammonia in 120 ml of ethanol.

Yield: 55% of theory.

EXAMPLE 261

The compound of Example 259 was also obtained analogously to Example 3 by heating a solution of 50 mmols of 3'-nitrobenzylideneacetoacetic acid benzyl ester and 50 mmols of 2-aminopent-2-en-4-one in 90 ml of ethanol.

Yield: 51% of theory.

EXAMPLE 262

The compound of Example 259 was also obtained analogously to Example 4 by heating a solution of 50 mmols of 3'-nitrobenzylideneacetoacetic acid benzyl ester, 50 mmols of acetylacetone and 66 ml of concentrated ammonia in 90 ml of ethanol.

Yield: 46% of theory.

EXAMPLE 264

The compound of Example 259 was also obtained analogously to Example 6 by heating a solution of 50 mmols of 2-aminopent-2-en-4-one, 50 mmols of 3-nirobenzaldehyde and 50 mmols of acetoacetic acid benzyl ester in 90 ml of ethanol.

Yield: 40% of theory.

EXAMPLES 265 to 270

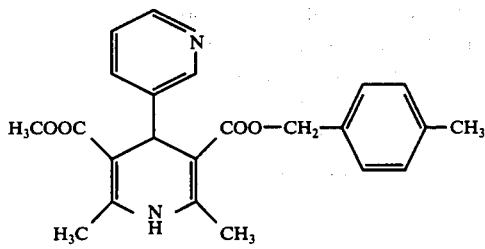

EXAMPLE 265

Analogously to Example 1 heating a solution of 75 mmols of pyridyl-3-methylideneacetoacetic acid methyl ester and 75 mmols of β-aminocrotonic acid 4-methylbenzyl ester in 120 ml of ethanol gave 2,6-dimethyl-3-methoxycarbonyl-4-(pyridyl-3)-1,4-dihydropyridine-5-carboxylic acid 4-methylbenzyl ester of melting point 175° C (from ethanol).
Yield: 65% of theory.

EXAMPLE 266

The compound of Example 265 was also obtained analogously to Example 2 by heating a solution of 75 mmols of pyridyl-3-methylideneacetoacetic acid methyl ester, 75 mmols of acetoacetic acid 4-methylbenzyl ester and 9 ml of concentrated ammonia in 120 ml of ethanol.
Yield: 58% of theory.

EXAMPLE 267

The compound of Example 265 was also obtained analogously to Example 3 by heating of solution of 50 mmols of pyridyl-3-methylideneacetoacetic acid 4-methylbenzyl ester and 50 mmols of β-aminocrotonic acid methyl ester in 90 ml of ethanol.
Yield: 60% of theory.

EXAMPLE 268

The compound of Example 265 was also obtained analogously to Example 4 by heating a solution of 50 mmols of pyridyl-3-methylideneacetoacetic acid 4-methylbenzyl ester, 50 mmols of acetoacetic acid methyl ester and 6 ml of concentrated ammonia in 90 ml of ethanol.
Yield: 52% of theory.

EXAMPLE 269

The compound of Example 265 was also obtained anaologously to Example 5 by heating a solution of 50 mmols of β-aminocrotonic acid 4-methylbenzyl ester, 50 mmols of pyridin-3-aldehyde and 50 mmols of acetoacetic acid methyl ester in 90 ml of ethanol.
Yield: 53% of theory.

EXAMPLE 270

The compound of Example 265 was also obtained analogously to Example 6 by heating a solution of 50 mmols of β-aminocrotonic acid methyl ester, 50 mmols of pyridin-3-aldehyde and 50 mmols of acetoacetic acid 4-methylbenzyl ester in 90 ml of ethanol.
Yield: 48% of theory.

EXAMPLES 271 TO 276

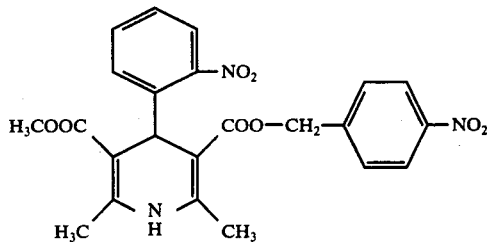

EXAMPLE 271

Analogously to Example 1 heating a solution of 75 mmols of 2'-nitrobenzylideneacetoacetic acid methyl ester and 75 mmols of β-aminocrotonic acid 4-nitrobenzyl ester in 120 ml of ethanol gave 2,6-dimethyl-3-methoxycarbonyl-4-(2'-nitrophenyl)-1,4-dihydropyridine-5-carboxylic acid 4-nitrobenzyl ester of melting point 156° C (from ethanol).
Yield: 75% of theory.

EXAMPLE 272

The compound of Example 271 was also obtained analogously to Example 2 by heating a solution of 75 mmols of 2'-nitrobenzylideneacetoacetic acid methyl ester, 75 mmols of acetoacetic acid 4-nitrobenzyl ester and 9 ml of concentrated ammonia in 120 ml of ethanol.
Yield: 62% of theory.

EXAMPLE 273

The compound of Example 271 was also obtained analogously to Example 3 by heating a solution of 50 mmols of 2'-nitrobenzylideneacetoacetic acid 4-nitrobenzyl ester and 50 mmols of β-aminocrotonic acid methyl ester in 90 ml of ethanol.
Yield: 64% of theory.

EXAMPLE 274

The compound of Example 271 was also obtained analogously to Example 4 by heating a solution of 50 mmols of 2'-nitrobenzylideneacetoacetic acid 4-nitrobenzyl ester, 50 mmols of acetoacetic acid methyl ester and 6 ml of concentrated ammonia in 90 ml of ethanol.
Yield: 58% of theory.

EXAMPLE 275

The compound of Example 271 was also obtained analogously to Example 5 by heating a solution of 50 mmols of β-aminocrotonic acid 4-nitrobenzyl ester, 50 mmols of acetoacetic acid methyl ester and 50 mmols of 2-nitrobenzyldehyde in 90 ml of ethanol.
Yield: 55% of theory.

EXAMPLE 276

The compound of Example 271 was also obtained analogously to Example 6 by heating a solution of 50 mmols of β-aminocrotonic acid methyl ester, 50 mmols of 2-nitrobenzaldehyde and 50 mmols of acetoacetic acid 4-nitrobenzyl ester in 90 ml of ethanol.
Yield: 51% of theory.

EXAMPLES 277 TO 282

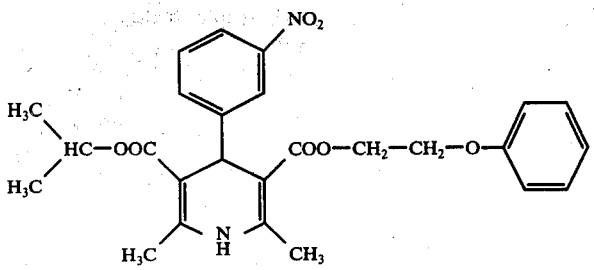

EXAMPLE 277

Analogously to Example 1 heating a solution of 75 mmols of 3'-nitrobenzylideneacetoacetic acid isopropyl ester and 75 mmols of β-aminocrotonic acid 2-phenoxyethyl ester in 120 ml of ethanol gave 2,6-dimethyl-3-isopropoxycarbonyl-4-(3'-nitrophenyl)-1,4-dihydropyridine-5-carboxylic acid 2-phenoxyethyl ester of melting point 110° C (from ethanol).

Yield: 70% of theory.

EXAMPLE 278

The compound of Example 277 was also obtained analogously to Example 2 by heating a solution of 75 mmols of 3'-nitrobenzylideneacetoacetic acid isopropyl ester, 75 mmols of acetoacetic acid 2-phenoxyethyl ester and 9 ml of concentrated ammonia in 120 ml of ethanol.

Yield: 61% of theory.

EXAMPLE 279

The compound of Example 277 was also obtained analogously to Example 3 by heating a solution of 50 mmols of 3'-nitrobenzylideneacetoacetic acid 2-phenoxyethyl ester and 50 mmols of β-aminocrotonic acid isopropyl ester in 90 ml of ethanol.

Yield: 68% of theory.

EXAMPLE 280

The compound of Example 277 was also obtained analogously to Example 4 by heating a solution of 50 mmols of 3'-nitrobenzylideneacetoacetic acid 2-phenoxyethyl ester, 50 mmols of acetoacetic acid isopropyl ester and 6 ml of concentrated ammonia in 90 ml of ethanol.

Yield: 55% of theory.

EXAMPLE 281

The compound of Example 277 was also obtained analogously to Example 5 by heating a solution of 50 mmols of β-aminocrotonic acid 2-phenoxyethyl ester, 50 mmols of 3-nitrobenzaldehyde and 50 mmols of acetoacetic acid isopropyl ester in 90 ml of ethanol.

Yield: 51% of theory.

EXAMPLE 282

The compound of Example 277 was also obtained analogously to Example 6 by heating a solution of 50 mmols of β-aminocrotonic acid isopropyl ester, 50 mmols of 3-nitrobenzaldehyde and 50 mmols of acetoacetic acid 2-phenoxyethyl ester in 90 ml of ethanol.

Yield: 48% of theory.

EXAMPLES 283 to 288

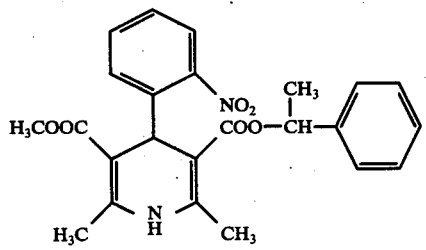

EXAMPLE 283

Analogously to Example 1 heating a solution of 75 mmols of 2'-nitrobenzylideneacetoacetic acid methyl ester and 75 mmols of β-aminocrotonic acid α-methylbenzyl ester in 120 ml of ethanol gave 2,6-dimethyl-3-methoxycarbonyl-4-(2'-nitrophenyl)-1,4-dihydropyridine-5-carboxylic acid α-methylbenzyl ester of melting point 154° C (from ethanol).

Yield: 60% of theory.

EXAMPLE 284

The compound of Example 283 was also obtained analogously to Example 2 by heating a solution of 75 mmols of 2'-nitrobenzylideneacetoacetic acid methyl ester, 75 mmols of acetoacetic acid α-methylbenzyl ester and 9 ml of concentrated ammonia in 120 ml of ethanol.

Yield: 49% of theory.

EXAMPLE 285

The compound of Example 283 was also obtained analogously to Example 3 by heating a solution of 50 mmols of 2'-nitrobenzylideneacetoacetic acid α-methylbenzyl ester and 50 mmols of β-aminocrotonic acid methyl ester in 90 ml of ethanol.

Yield: 52% of theory.

EXAMPLE 286

The compound of Example 283 was also obtained analogously to Example 4 by heating a solution of 50 mmols of 2'-nitrobenzylideneacetoacetic acid α-methylbenzyl ester, 50 mmols of acetoacetic acid methyl ester and 6 ml of concentrated ammonia in 90 ml of ethanol.

Yield 44% of theory.

EXAMPLE 287

The compound of Example 283 was also obtained analogously to Example 5 by heating a solution of 50 mmols of β-aminocrotonic acid α-methylbenzyl ester, 50 mmols of 2-nitrobenzaldehyde and 50 mmols of acetoacetic acid methyl ester in 90 ml of ethanol.

Yield: 40% of theory.

EXAMPLE 288

The compound of Example 283 was also obtained analogously to Example 6 by heating a solution of 50 mmols of β-aminocrotonic acid methyl ester, 50 mmols of 2-nitrobenzaldehyde and 50 mmols of acetoacetic acid α-methylbenzyl ester in 90 ml of ethanol.

Yield: 33% of theory.

EXAMPLES 289 to 294

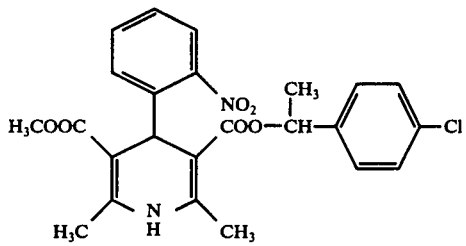

EXAMPLE 289

Analogously to Example 1 heating a solution of 75 mmols of 2'-nitrobenzylideneacetoacetic acid methyl ester and 75 mmols of β-aminocrotonic acid α-methyl-4-chlorobenzyl ester in 120 ml of ethanol gave 2,6-dimethyl-3-methoxycarbonyl-4-(2'-nitrophenyl)-1,4-dihydropyridine-5-carboxylic acid α-methyl-4-chlorobenzyl ester of melting point 206° C (from ethanol).

Yield: 56% of theory.

EXAMPLE 290

The compound of Example 289 was also obtained analogously to Example 2 by heating a solution of 75 mmols of 2'-nitrobenzylideneacetoacetic acid methyl ester, 75 mmols of acetoacetic acid α-methyl-4-chlorobenzyl ester and 9 ml of concentrated ammonia in 120 ml of ethanol.

Yield: 48% of theory.

EXAMPLE 291

The compound of Example 289 was also obtained analogously to Example 3 by heating a solution of 50 mmols of 2'-nitrobenzylideneacetoacetic acid α-methyl-4-chlorobenzyl ester and 50 mmols of β-aminocrotonic acid methyl ester in 90 ml of ethanol.

Yield: 45% of theory.

EXAMPLE 292

The compound of Example 289 was also obtained analogously to Example 4 by heating a solution of 50 mmols of 2'-nitrobenzylideneactoacetic acid α-methyl-4-chlorobenzyl ester, 50 mmols of acetoacetic acid methyl ester and 6 ml of concentrated ammonia in 90 ml of ethanol.

Yield: 38% of theory.

EXAMPLE 293

The compound of Example 289 was also obtained analogously to Example 5 by heating a solution of 50 mmols of β-aminocrotonic acid α-methyl-4-chlorobenzyl ester, 50 mmols of 2-nitrobenzaldehyde and 50 mmols of acetoacetic acid methyl ester in 90 ethanol.

Yield: 35% of theory.

EXAMPLE 294

The compound of Example 289 was also obtained analogously to Example 6 by heating a solution of 50 mmols of β-aminocrotonic acid methyl ester, 50 mmols of 2-nitrobenzaldehyde and 50 mmols of acetoacetic acid α-methyl-4-chlorobenzyl ester in 90 ml of ethanol.

Yield: 31% of theory.

What is claimed is:

1. A compound of the formula:

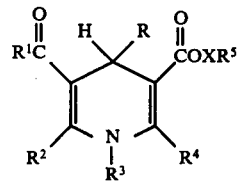

wherein
is a phenyl group, unsubstituted or substituted with from one to three sterically permissible substituents selected from the group consisting of lower alkyl of 1 to 6 carbon atoms, alkoxy of 1 to 6 carbon atoms, halo, trifluoromethyl, nitro, azido, cyano, hydroxy, amino, carbo(lower alkoxy) wherein lower alkoxy contains from 1 to 6 carbon atoms, carbamido, sulfonamido, (lower alkyl)thio of 1 to 6 carbon atoms, (lower alkyl)sulfinyl of 1 to 6 carbon atoms or (lower alkyl)sulfonyl of 1 to 6 carbon atoms, or naphthyl;

$R^1$ is lower alkoxy of 1 to 6 carbon atoms, cycloalkoxy of 3 to 7 carbon atoms or (lower alkoxy)lower alkoxy wherein each lower alkoxy contains 1 to 6 carbon atoms;

each of $R^2$ and $R^4$, independently of the other is hydrogen or lower alkyl of 1 to 6 carbon atoms;

$R^3$ is hydrogen, lower alkyl of 1 to 6 carbon atoms or (lower alkoxy)lower alkyl wherein each of lower alkoxy and lower alkyl contain 1 to 6 carbon atoms;

$R^5$ is a phenyl, phenoxy or phenylthio group unsubstituted or substituted with from one to three sterically permissible substituents selected from the group consisting of lower alkyl of 1 to 6 carbon atoms, lower alkoxy of 1 to 6 carbon atoms, halo, trifluoromethyl, hydroxy, amino, di(lower alkyl)amino wherein each lower alkyl contains 1 to 6 carbon atoms, nitro, cyano, carbamido, sulfonamido, (lower alkyl)thio of 1 to 6 carbon atoms, (lower alkyl)sulfinyl of 1 to 6 carbon atoms, a (lower alkyl) sulfonyl of 1 to 6 carbon atoms; and X is lower alkylene of 1 to 6 carbon atoms.

2. A compound according to claim 1 wherein

R is phenyl or phenyl unsubstituted or substituted with lower alkyl, lower alkoxy, halo, trifluoromethyl, nitro, azido or cyano;

$R^1$ is lower alkoxy, cycloalkoxy or (lower alkoxy)-lower alkoxy;

each of $R^2$ and $R^4$ is methyl;

$R^3$ is hydrogen or methyl;

$R^5$ is a phenyl or phenoxy group unsubstituted or substituted with one to three sterically permissible substituents selected from the group consisting of lower alkyl, lower alkoxy, halo, trifluoromethyl and nitro; and X is lower alkylene.

3. A compound according to claim 1 wherein

R is phenyl, nitrophenyl, trifluoromethylphenyl, chlorophenyl or cyanophenyl;

$R^1$ is methoxy, ethoxy, isopropoxy, isobutoxy, cyclopentoxy, cyclohexoxy or methoxyethoxy;

each of $R^2$ and $R^4$ is methyl;

$R^3$ is hydrogen or methyl;

$R^5$ is phenoxy, phenyl, chlorophenyl, dichlorophenyl, methylphenyl, t.-butylphenyl, methoxyphenyl, dimethoxyphenyl, trimethoxyphenyl, triflouoromethylphenyl or nitrophenyl; and X is methylene, ethylene, ethylidene, trimethylene or 1,2-propylene.

4. A compound according to claim 1 wherein

R is phenyl or nitrophenyl;

$R^1$ is methoxy or isopropoxy;

each of $R^2$ and $R^4$ is methyl;

$R^3$ is hydrogen;

$R^5$ is phenyl, chlorophenyl or trifluoromethylphenyl; and

X is methylene.

5. A compound according to claim 1 wherein

R is 2-nitrophenyl or 3-nitrophenyl;

$R^1$ is methoxy or isopropoxy;

each of $R^2$ and $R^4$ is methyl;

$R^3$ is hydrogen;

$R^5$ is phenyl, 3-chlorophenyl, 4-chlorophenyl, 3-trifluoromethylphenyl or 4-trifluoromethylphenyl; and X is methylene.

6. The compound according to claim 1 which is 2,6-dimethyl-3-methoxycarbonyl-4-(2'-nitrophenyl)-1,4-dihydropyridine-5-carboxylic acid benzyl ester.

7. The compound according to claim 1 which is 2,6-dimethyl-3-methoxycarbonyl-4-(2'-nitrophenyl)-1,4-dihydropyridine-5-carboxylic acid 4-chlorobenzyl ester.

8. The compound according to claim 1 which is 2,6-dimethyl-3-methoxycarbonyl-4-(2'-nitrophenyl)-1,4-dihydropyridine-5-carboxylic acid 3,4-dichlorobenzyl ester.

9. The compound according to claim 1 which is 2,6-dimethyl-3-methoxycarbonyl-4-(2'-nitrophenyl)-1,4-dihydropyridine-5-carboxylic acid 4-methylbenzyl ester.

10. The compound according to claim 1 which is 2,6-dimethyl-3-methoxycarbonyl-4-(3'-nitrophenyl)-1,4-dihydropyridine-5-carboxylic acid 3-chlorobenzyl ester.

11. The compound according to claim 1 which is 2,6-dimethyl-3-isopropoxycarbonyl-4(3'-nitrophenyl)-1,4-dihydropyridine-5-carboxylic acid benzyl ester.

12. The compound according to claim 1 which is 2,6-dimethyl-3-isopropoxycarbonyl-4-(3'-nitrophenyl)-1,4-dihydropyridine-5-carboxylic acid 4-chlorobenzyl ester.

13. The compound according to claim 1 which is 2,6-dimethyl-3-isopropoxycarbonyl-4(3'-nitrophenyl)-1,4-dihydropyridine-5-carboxylic acid 3,4-dichlorobenzyl ester.

14. The compound according to claim 1 which is 2,6-dimethyl-3-isopropoxycarbonyl-4-(3'-nitrophenyl)-1,4-dihydropyridine-5-carboxylic acid 3-chlorobenzyl ester.

15. The compound according to claim 1 which is 2,6-dimethyl-3-isopropoxycarbonyl-4-(3'-nitrophenyl)-1,4-dihydropyridine-5-carboxylic acid 2-chlorobenzyl ester.

16. The compound according to claim 1 which is 2,6-dimethyl-3-(2-methoxyethyloxy)-carbonyl-4-(3'-nitrophenyl)-1,4-dihydropyridine-5-carboxylic acid benzyl ester.

17. The compound according to claim 1 which is 2,6-dimethyl-3-(2-methoxyethyloxy)-carbonyl-4-(3'-nitroethyl)-5-carboxylic acid 1-phenylethyl ester.

18. The compound according to claim 1 which is 2,6-dimethyl-3-(2-methoxyethyloxy)-carbonyl-4-(3'-nitrophenyl)-1,4-dihydropyridine-5-carboxylic acid 1-(4-chlorophenyl)-ethyl ester.

19. The compound according to claim 1 which is 2,6-dimethyl-3-methoxycarbonyl-4-(3'-nitrophenyl)-1,4-dihydropyridine-5-carboxylic acid 4-trifluoromethylbenzyl ester.

20. The compound according to claim 1 which is 2,6-dimethyl-3-isopropoxycarbonyl-4-(3'-nitrophenyl)-1,4-dihydropyridine-5-carboxylic acid 4-trifluoromethylbenzyl ester.

21. The method of producing coronary dilating, spasmolytic and hypotensive effects in humans and other animals which comprises orally, parenterally or perlingually administering thereto an effective amount of a compound according to claim 1.

22. An oral, parenteral or perlingual pharmaceutical composition for producing coronary dilating, spasmolytic and hypotensive effects in humans or other animals comprising an effective amount of a compound according to claim 1 in combination with a pharmaceutical carrier.

* * * * *